US012707185B2

(12) United States Patent
Forster et al.

(10) Patent No.: US 12,707,185 B2
(45) Date of Patent: Aug. 11, 2026

(54) SYSTEMS AND METHODS FOR FUNCTIONAL ADJUSTMENTS OF PERSONAL PROTECTIVE EQUIPMENT

(71) Applicant: 3M INNOVATIVE PROPERTIES COMPANY, St. Paul, MN (US)

(72) Inventors: Jan D. Forster, Aachen (DE); Frank T. Herfort, Korschenbroich (DE); Vijay K. Gidla, Värnamo (SE); Abel Gladstone Mangam, Värnamo (SE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 275 days.

(21) Appl. No.: 18/558,549

(22) PCT Filed: Apr. 28, 2022

(86) PCT No.: PCT/IB2022/053955
§ 371 (c)(1),
(2) Date: Nov. 2, 2023

(87) PCT Pub. No.: WO2022/234406
PCT Pub. Date: Nov. 10, 2022

(65) Prior Publication Data

US 2024/0244363 A1 Jul. 18, 2024

Related U.S. Application Data

(60) Provisional application No. 63/201,543, filed on May 4, 2021.

(51) Int. Cl.

| | |
|---|---|
| ***A61F 9/06*** | (2006.01) |
| ***A61F 11/14*** | (2006.01) |
| ***H04R 1/10*** | (2026.01) |

(52) U.S. Cl.
CPC ............ *H04R 1/1083* (2013.01); *A61F 9/06* (2013.01); *A61F 11/145* (2022.01)

(58) Field of Classification Search
CPC ........... H04R 1/1083; H04R 2201/107; H04R 2420/07; A61F 9/06; A61F 11/145
(Continued)

(56) References Cited

U.S. PATENT DOCUMENTS

2015/0222977 A1 8/2015 Angel, Jr.
2016/0269841 A1* 9/2016 Shinde ................ H04R 1/1041
(Continued)

FOREIGN PATENT DOCUMENTS

CN 104394491 B 1/2018
EP 3008920 B1 8/2020
(Continued)

OTHER PUBLICATIONS

Fast switching between welding and grinding—Facebook Video, Mar. 17, 2015, 1 Page.
(Continued)

*Primary Examiner* — Carolyn R Edwards
*Assistant Examiner* — Friedrich Fahnert
(74) *Attorney, Agent, or Firm* — Katherine M. Scholz

(57) ABSTRACT

A personal protective equipment device is presented. The PPE device includes a microphone configured to capture an ambient sound stream. The PPE device also includes a sound analyzer that receives the ambient sound stream and characterizes a sound fingerprint around the device based on the ambient sound stream. The PPE device also includes a function preset selector that, based on the characterized sound fingerprint, selects a function preset. The PPE device also includes a function preset implementor that implements the function preset in response to an event trigger. Imple-
(Continued)

menting the function preset includes adjusting a functional setting of a device from a first setting to a second setting.

18 Claims, 12 Drawing Sheets

(58) Field of Classification Search
USPC ........................................................... 381/72
See application file for complete search history.

(56) References Cited

U.S. PATENT DOCUMENTS

| | | | | |
|---|---|---|---|---|
| 2019/0130926 | A1* | 5/2019 | Giri | G10L 17/02 |
| 2021/0126972 | A1* | 4/2021 | Lobner | G08B 21/02 |

FOREIGN PATENT DOCUMENTS

| | | | |
|---|---|---|---|
| GB | 2456296 | B | 2/2012 |
| WO | 2016022905 | A1 | 2/2016 |
| WO | 2019166296 | A1 | 9/2019 |
| WO | 2021064658 | A1 | 4/2021 |
| WO | 2022234384 | A1 | 11/2022 |

OTHER PUBLICATIONS

International Search report for PCT International Application No. PCT/IB2022/53955, mailed on Jul. 7, 2022, 5 pages.

* cited by examiner

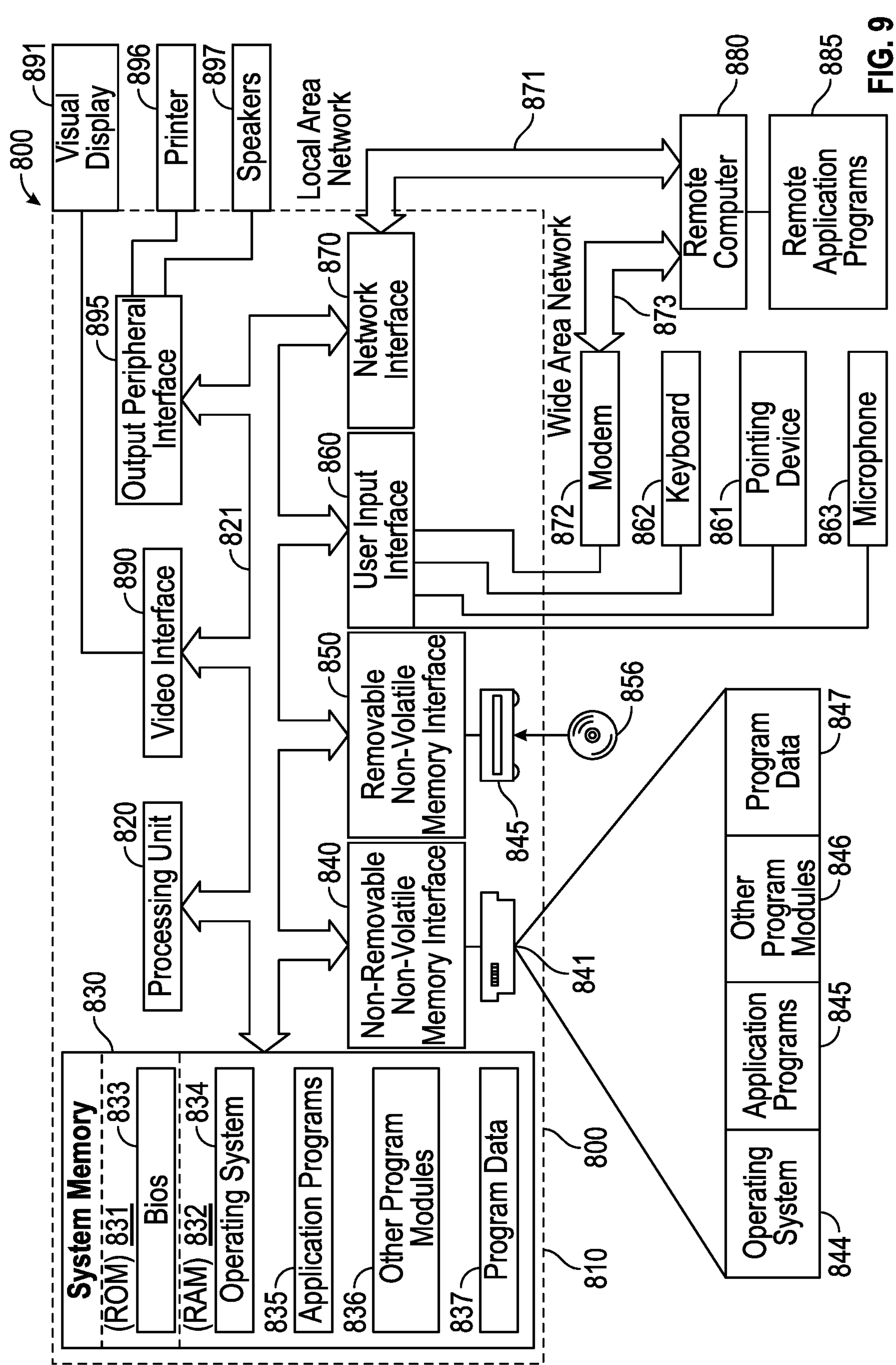
800
Visual Display
891
Printer
896
Speakers
897
Local Area Network
871
Remote Computer
880
Remote Application Programs
885
FIG. 9
Output Peripheral Interface
895
Network Interface
870
Wide Area Network
873
Modem
872
Keyboard
862
Pointing Device
861
Microphone
863
User Input Interface
860
Video Interface
890
821
Processing Unit
820
Removable Non-Volatile Memory Interface
850
856
845
Non-Removable Non-Volatile Memory Interface
840
841
Operating System
844
Application Programs
845
Other Program Modules
846
Program Data
847
830
System Memory
(ROM) 831
Bios
833
(RAM) 832
Operating System
834
Application Programs
835
Other Program Modules
836
Program Data
837
800
810

SYSTEMS AND METHODS FOR FUNCTIONAL ADJUSTMENTS OF PERSONAL PROTECTIVE EQUIPMENT

CROSS REFERENCE TO RELATED APPLICATIONS

This application is a national stage filing under 35 U.S.C. 371 of PCT/IB2022/053955, filed Apr. 28, 2022, which claims the benefit of U.S. Provisional Application No. 63/201,543, filed May 4, 2021, the disclosure of which is incorporated by reference in its entirety herein.

BACKGROUND

Maintaining the safety and health of workers is a major concern across many industries. Various rules and regulations have been developed to aid in addressing this concern. Such rules provide sets of requirements to ensure proper administration of personnel health and safety procedures. To help in maintaining worker safety and health, some individuals may be required to don, wear, carry, or otherwise use a personal protective equipment (PPE) article, if the individuals enter or remain in work environments that have hazardous or potentially hazardous conditions.

Consistent with evolving rules and regulations related to safety, safety is an important concern in any workplace requiring the use of PPE. Companies or businesses employing workers wearing articles of PPE also want to ensure that workers are complying with relevant laws, regulations and company policies related to proper use and maintenance of PPE.

SUMMARY

A personal protective equipment device is presented. The PPE device includes a microphone configured to capture an ambient sound stream. The PPE device also includes a sound analyzer that receives the ambient sound stream and characterizes a sound fingerprint around the device based on the ambient sound stream. The PPE device also includes a function preset selector that, based on the characterized sound fingerprint, selects a function preset. The PPE device also includes a function preset implementor that implements the function preset in response to an event trigger. Implementing the function preset includes adjusting a functional setting of a device from a first setting to a second setting.

Systems and methods herein provide an improved user experience through automized settings for a user of a PPE device, allowing for adjustment of incoming sounds based on a detected environment around the user. For example, in areas where the user may need to be more alert to their surroundings (such as a dangerous area), volume of music or radio may be decreased or turned off. However, if the user then moves into a safer area, the volume may be restored. Adjustments may be made manually or automatically. Systems and methods herein provide an improved, customizable audio experience for users.

The details of one or more examples of the disclosure are set forth in the accompanying drawings and the description below. Other features, objects, and advantages of the disclosure will be apparent from the description and drawings, and from the claims.

BRIEF DESCRIPTION OF THE DRAWINGS

FIGS. 7-9 illustrate example devices that can be used in embodiments herein.

DETAILED DESCRIPTION

Many types of personal protective equipment (PPE) include a speaker, a microphone, or both. The speakers may provide a received audio transmission to a user, while the microphones may capture audio from the wearer. Different forms of PPE have different quality microphones and speakers. Additionally, wearing different PPE interferes with the ability of microphones to pick up audio, and for speakers to transmit audio.

Some hearing protection devices include active hearing protection, which includes one or more microphones that receive ambient sound from a user's surroundings, a processor to process the sound to a safe level, and one or more speakers to play it back, at the safe level, to a user. Active hearing protection devices use electronic circuitry to pick up ambient sound through the microphone and convert them to safe levels before playing it back to the user through a speaker. At least some embodiments herein are applicable to active hearing devices.

Some active hearing protection units are level dependent, such that an electronic circuit adapts the sound pressure level. Level dependent hearing protection may include filtering out or clipping sound above a given sound pressure level, for example actively reducing the sound of a gunshot to a safe sound level. Level dependent hearing protection units help to filter out impulse noises, such as gunshots from surrounding noises, and/or continuously adapt all ambient sound received to an appropriate level before it is reproduced to a user. In a level dependent active hearing protection system, a sound signal is first received by a microphone. The received sound signal is converted to an electronic signal for processing. After processing the sound signal such that all frequencies are at safe levels for a user, the sound signal is reproduced and played back to a user through a speaker of the hearing protection device.

Active hearing protection units, specifically level dependent active hearing protection units, may be necessary to facilitate communication in noisy environments, or environments where noise levels can vary significantly, or where high impulse sounds may cause hearing damage. A user may need to hear nearby ambient sounds, such as machine sounds or speech, while also being protected from harmful noise levels.

However, while hearing protection units are illustrated and described herein as one example PPE device that may benefit from systems and methods herein, it is expressly contemplated that many types of PPE may include microphones, or communicate with devices that include microphones capable of capturing ambient sound.

Figure 1:
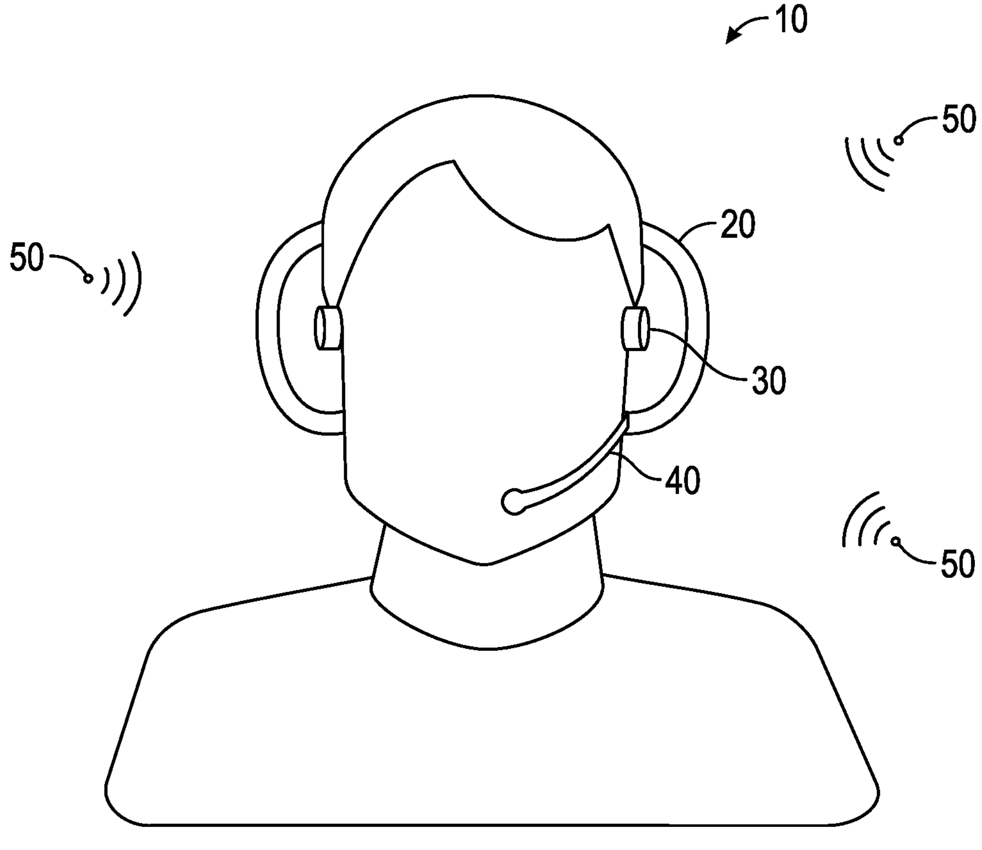
FIG. 1 illustrates a user of a hearing protection device.

As illustrated in FIG. 1, active hearing protection units can be provided using either ear plugs or ear-muff designs, or in a dual protection mode, as described in U.S. Provisional Patent Application with Ser. No. 62/909,989, filed Oct. 3, 2019, which is herein incorporated by reference.

In many environments, it may be helpful to adjust functional device settings (e.g. PPE) based on a surrounding environment. For example, while in a battlefield scenario, it may be desired for a PPE to amplify incoming audio from other PPE (e.g. other human speech) and decrease environmental sound. Similarly, in a construction scenario, it may be a safety concern to play radio or music above a certain level so, as a user enters the construction zone, music may be reduced to a 'safe' maximum that allows the user to hear other sounds that may indicate danger.

A system is desired that can recognize an environment based on an incoming sound stream and adjust functional settings of a PPE device based on the detected environment. For example, if it is detected that a grinding operation is nearby, the ADF (auto darkening filter) mode of a Speedglas™ welding helmet is switched to a grinding mode. Or a Versaflow™ PAPR (powered air purifying respirator) may increase a rate of air flow if a hot working environment is detected.

Currently, it can be known where a worker is in an environment using WiFi™, beacons or GPS (mainly useful outdoors). However, that requires PPE devices to be WiFi™, Bluetooth or GPS-enabled and/or beacons to be operational. Additionally, it may also require PPE devices to be communicably interconnected. Systems and methods herein allow for individual PPE devices to determine an environment and adjust settings based on the determination.

Systems and methods herein may also provide improved protection over beacon-based systems as sound-fingerprinting can provide highly accurate guesses as to an environment, which the PPE can then use as the basis for automatically adjusting system settings.

It is known in the prior art that a sound can be recognized and an alert provided thereabout, for example as described in U.S. PAP 2015/0222977, published on Aug. 6, 2015. Additionally, it is known in the prior art that a device can match a received sound to a registered sound pattern to generate an alert, as described in U.S. PAP 2016/0269841, published on Sep. 15, 2016. However, it has not previously been known to detect an environment, activity or task based on incoming sounds and, based on the environment identification, adjust functional settings, like volume or brightness, automatically in response to the detected environment.

FIG. 1 illustrates a dual hearing protection system in accordance with an embodiment of the present invention. However, while a dual hearing system 10 is illustrated, it is expressly contemplated that embodiments herein could include either earmuffs 20 or inner ear plugs 30, operating alone. Similarly, systems and methods herein may also be incorporated into other PPE devices on which microphones can be mounted or placed to capture ambient environmental sound. Additionally, in some embodiments, a user may have two devices that are communicably coupled. For example, in-ear hearing protection units may have a microphone for capturing ambient sounds, and may be communicably coupled to a PAPR unit. Based on sounds detected by the microphone, it may be detected that a wearer of the two PPE items has entered a smelter, known for being in a hot area. Therefore, as described herein, a command may be sent to the PAPR to increase air flow, either directly from the hearing protection unit or through a central communication unit.

A person 10 may be in an environment with a plurality of sounds 50. As illustrated in FIG. 1, different sounds 50 may have different sound pressure levels associated with them. Some of sounds 50 may be sounds that user 10 wants to hear, and may want amplified. Some other sounds 50 may be sounds that could distract a user 10, which a user may want reduced or cancelled altogether. Some sounds 50 may be indicative of an environment, or of a danger to a PPE wearer.

A PPE can also include one or more microphones 40. Microphone 40 is illustrated in FIG. 1 as positioned to pick up the voice of user 10. However, other microphones (not shown) may be positioned to pick up ambient sounds 50. Additionally, each of first and second hearing protection systems 20, 30 may have one or more microphones 40.

Figure 2:
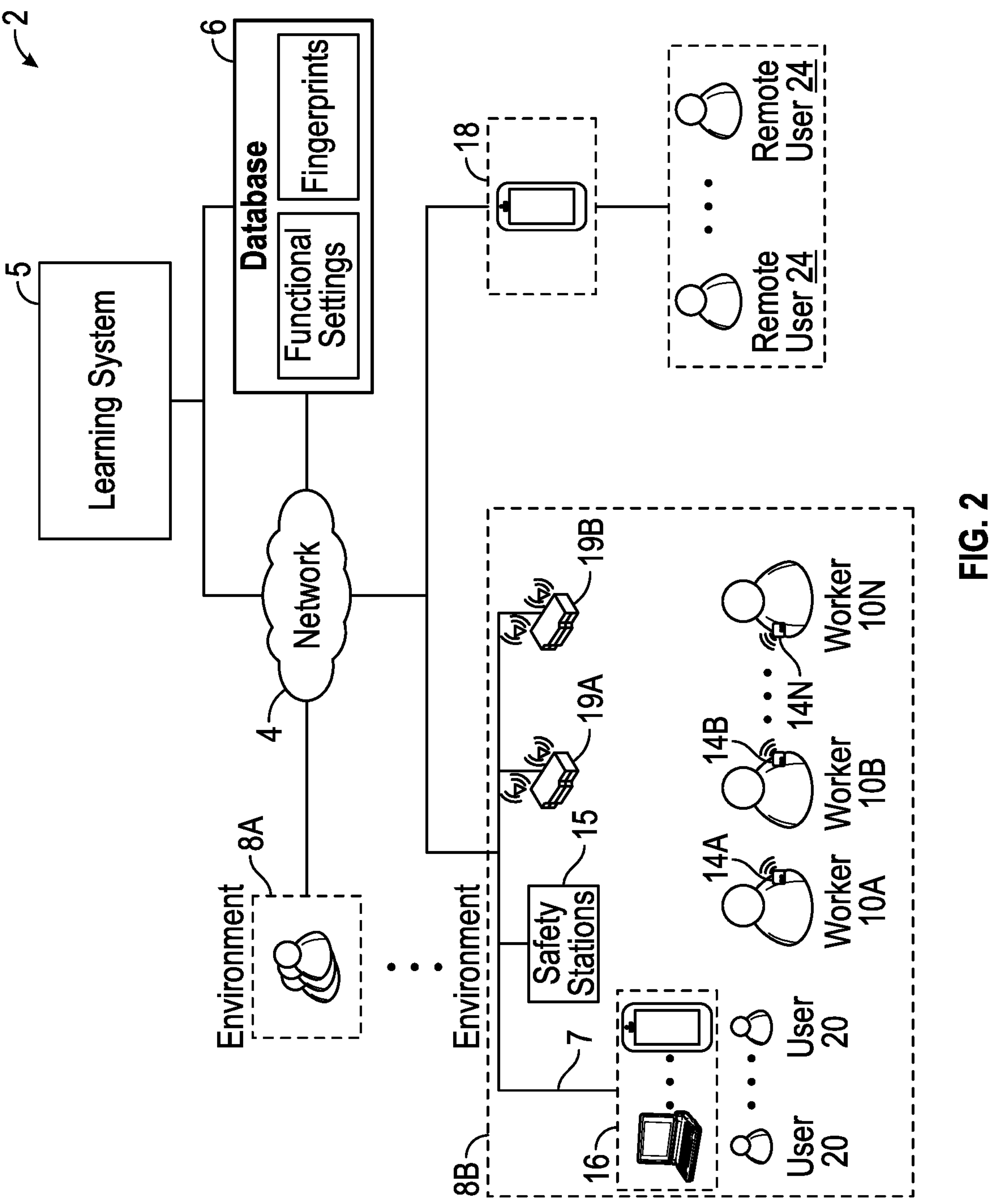
FIG. 2 illustrates a worksite in which embodiments of the present invention may be useful.

FIG. 2 illustrates a worksite in which embodiments of the present invention may be useful. FIG. 2 is a block diagram illustrating an example networked environment 2 for a worksite 8A or 8B. The worksite environments 8A and 8B may have one or more workers 10A-10N, each of which may be wearing different PPE, such as the hearing protection described with respect to FIG. 1. Workers 10A-10N may all be in the same environment 2, but they may each be performing a variety of tasks. Environment 8A may have a different collection of sounds than Environment 8B. For example, 8A may be a loading dock with sounds of trucks and loading equipment. Environment 8B may be a machining area with sounds of grinding.

Environment 2 includes a database 6 which includes environment indicia, including environmental fingerprints, and functional adjustments for different environments that may be accessed by PPE worn by users 10A-10N or may be downloaded into the PPE devices. For example, as described herein, individual functional adjustments may be associated with different environments and may be accessed by a processor of a PPE device when a given environment is detected, so that the functional change can be applied. The environment indicia and associated functional adjustments may be accessible from a local storage, within a PPE device, or may be downloaded from/accessible from a remote storage source, such as an online database. The environment indicia may be associated with a known area, e.g. a forward loading dock, or with a general environment, e.g. one with moving vehicles and heavy machinery. For example, an environmental indicia may be an environmental fingerprint that includes one or more sounds expected in a given area, such as the sound of an arc welder in operation in a welding environment, the sound of a smelter in operation in a smelting environment, or the sounds of trucks moving in a loading dock.

Each of physical environments 8A and 8B represents a physical environment, such as a work environment, in which one or more individuals, such as workers 10, utilize personal protection equipment (PPE) while engaging in tasks or activities within the respective environment.

In this example, environment 8A is shown as generally as having workers 10, while environment 8B is shown in expanded form to provide a more detailed example. In the example of FIG. 2, a plurality of workers 10A-10N may be wearing a variety of different PPE, such as ear muff hearing protectors, in-ear hearing protectors, hard hats, gloves, glasses, goggles, masks, respirators, hairnets, scrubs, or any other suitable personal protective equipment.

While an environment 2 is illustrated as a plant or industrial environment, it is also expressly contemplated that, in some embodiments, a model database may be accessible to a single user, with a single PPE device, such as a handyman operating a power tool alone during a home remodel project.

In general, database 6, as described in greater detail herein, is configured to house environmental indicia and corresponding functional adjustments available for download by PPE within environments 8A and 8B. The environment indicia and corresponding functional adjustments may be generated by manufacturers of the PPE, manufactures of devices (e.g. manufacturers of power tools), other third parties, or individuals who create and upload their own preferred functional adjustments to database 6. Environmental indicia includes environment fingerprints that can be used as the basis to compare ambient sound to. An environment fingerprint may include one or more sounds or reductions of the existing sounds to specific characteristics, as described in FIG. 11C, for example, indicative of a particular environment, such as machinery noises, truck noises, grinding equipment, water, gun shots, etc. Database 6 may be accessed, through network 4, to one or more devices or displays 16 within an environment, or devices or displays 18, remote from an environment. For example, devices 16, 18 may have an application interface that allows a user 10A-10N to select potential environments they may encounter from database 6 for download to a PPE device. For example, an industrial worker may select environmental fingerprints and corresponding functional changes for a loading dock, cafeteria, office space as well as specific industrial zones or activities they may encounter, such as welding, smelting, etc.

As described herein, environmental indicia include both indications of physical locations, such as a smelter or a loading dock, as well as indications of activities, such as sounds of a moving truck, welding torch, chain saw, etc.

Additionally, the interface may also allow a user 10A-10N to upload an ambient sound to database 6, characterize it as an environmental fingerprint and create a functional adjustment that can be applied when that environmental indication is detected. The user 10A-10N may then be able to download the created/selected environmental fingerprint and functional adjustment to a PPE device such that the adjustment is applied when the environmental fingerprint is detected in the future. In some embodiments, PPE devices do not have the ability to download environmental fingerprints and associated functional adjustments directly from database 6. In other embodiments, PPE devices can access database 6 to download environmental fingerprints and functional adjustments, or to upload sounds directly. For example, if a sound is received that is not recognized by a given PPE device to correspond with a known environmental fingerprint, it may provide the sound to database 6 for recognition. Database 6 may have a greater database of environment fingerprints and may be able to provide a functional adjustment to the PPE device for application based on a match to an environmental fingerprint, when detected. Said functional adjustment may be automatically provided to a PPE through network 4, in one embodiment. In another embodiment, PPE may receive new environmental fingerprints and functional adjustments through a device 16, 18.

In some embodiments herein, a PPE device may include one or more of embedded sensors, communication components, monitoring devices and processing electronics. In addition, each article of PPE may include one or more output devices for outputting data that is indicative of operation of the PPE and/or generating and outputting communications to the respective worker 10. For example, PPE may include one or more devices to generate audible feedback (e.g., one or more speakers), visual feedback (e.g., one or more displays, light emitting diodes (LEDs) or the like), or tactile feedback (e.g., a device that vibrates or provides other haptic feedback). Additionally, PPE herein include processors capable of identifying an environment based on ambient sound, retrieve an environmental fingerprint and associated functional adjustment based on the identified sound, and apply the model to the PPE device, which may include automatically adjusting PPE device functional settings.

In some examples, each of environments 8 include computing facilities, such as displays 16, or through associated PPEs, by which workers 10 can communicate with model database 6. For examples, environments 8 may be configured with wireless technology, such as 802.11 wireless networks, Bluetooth® networks, 802.15 ZigBee networks, and the like. In the example of FIG. 2, environment 8B includes a local network 7 that provides a packet-based transport medium for communicating with PPE computing system 6 via network 4. In addition, environment 8B includes a plurality of wireless access points 19A, 19B that may be geographically distributed throughout the environment to provide support for wireless communications throughout the work environment.

In example implementations, an environment, such as environment 8B, may also include one or more safety stations 15 distributed throughout the environment. Safety stations 15 may allow one of workers 10 to check out articles of PPE and/or other safety equipment, verify that safety equipment is appropriate for a particular one of environments 8, and/or exchange data. For example, safety stations 15 may transmit alert rules, software updates, or firmware updates to articles of PPE or other equipment. Safety stations 15 may also include an I/O device that allows a user to interactively update stored environmental fingerprints and functional settings for their PPE and/or other devices. For example, a safety station 15, or another device, may have a keyboard/mouse and/or a touchscreen display that allows a user to see available environmental fingerprints/functional settings for different devices.

In addition, each of environments 8 include computing facilities that provide an operating environment for end-user computing devices 16 for interacting with model database 6 via network 4. For example, each of environments 8 typically includes one or more safety managers or supervisors, represented by users 20 or remote users 24, are responsible for overseeing safety compliance within the environment. For example, the end-user computing devices 16, 18 may be laptops, desktop computers, mobile devices such as tablets or so-called smart cellular phones.

Systems and methods herein allow for each PPE device to customize and improve an experience of each worker 10A-10N. Each worker, by downloading anticipated environmental fingerprints and functional adjustments from database 6, can have tailored PPE settings based on recognizing an environment using incoming sounds within a stream of sounds entering a microphone of a PPE device worn by the worker. In some embodiments, a worker may be able to create environmental fingerprints and select associated functional setting adjustments through a learning process of the PPE device.

Figure 3:
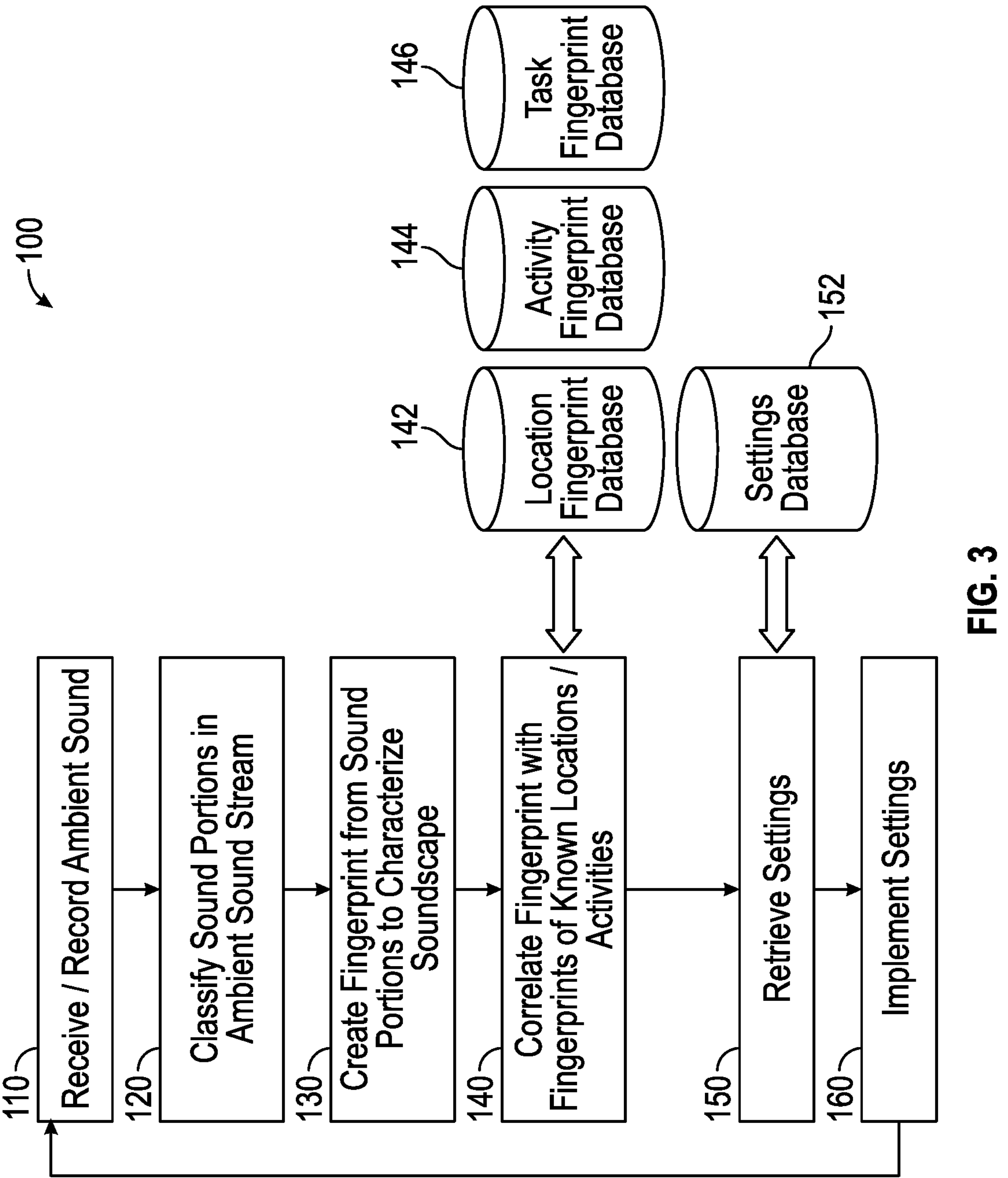
FIG. 3 illustrates a method of modifying sound settings of a PPE device in an embodiment of the present invention.

FIG. 3 illustrates a method of modifying sound settings of a PPE device in an embodiment of the present invention.

Method 100 is useful for quickly adjusting settings on a PPE device based on a detected environment. The environment is detected by identifying and characterizing sounds in an incoming stream of ambient sound and comparing it to known environmental fingerprints.

In some embodiments, method 100 is used in a known worksite—for example one with several areas each with known characteristics. For example, if an incoming sound stream includes 80% truck noise, 15% construction-related noise, and 5% human voices, it can be characterized as matching "Zone A"—which may be matched to a loading zone which has a fingerprint of 78% truck noise, 16% construction-related noise and 6% human voices. A match may not need to be exact, just a most likely match between a sound fingerprint and a database of environmental fingerprints. Once the match is made, the PPE device may automatically implement functionality changes based on the match. For example, a volume of FM radio or music may be decreased while a volume of ambient sound may be increased and a volume of incoming audio from other workers over radio may be increased.

In other embodiments, method 100 is used in an unknown environment. In such an instance, an incoming audio stream has 80% truck noise, 15% tool/equipment related noise and 5% human voices it may be characterized as a construction zone because it matches an environmental fingerprint of a construction zone retrieved from an environmental fingerprint database. Based on the identification, a PPE device may reduce volume of recreational sound (e.g. FM radio), increase the sound from other communication devices (e.g. radio communications from other PPE devices) and may provide an audible, visual or haptic indication that the worker is now entering a more dangerous zone. As discussed herein, the response to an identified environment may be set by a user, by a PPE manufacturer, PPE owner, or another source.

In block 110, ambient sound is received. The ambient sound is indicative of an environment around a wearer of a PPE device. The ambient sound may be received by a microphone associated with the wearer or with the PPE device. The microphone may be a boom microphone or another microphone that also picks up speech from a wearer. The microphone may, in other embodiments, be a dedicated microphone that periodically samples ambient sound for classification purposes according to method 100.

In block 120, one or more sound portions in the ambient sound stream are classified. For example, a jackhammer may be identified as well as human speech. The sound portions may be identified, for example, by referencing a sound database as described in U.S. Provisional Application No. 63/201,539. In another example, it may also be possible to recognize an environment based on previous device experience. For example, a range of sound classes may be provided—such as the sound of jackhammer, grinder, hammer, chain saw, circular saw, hydraulic press, human voice, alert signals etc.

If a device utilizing the system is worn by a user during an open air hard-rock concert, the system can create a fingerprint, even though none of the stored sound classes include guitar solos or drums. The system may find reasonably strong representations of some classes, whether or not the sound class source (e.g. jackhammer) are actually present and create a fingerprint based on the representations. The same environment will be detected next time the system detects a close enough match to the fingerprint, and the same associated settings may be applied.

In block 130, a sound fingerprint for the area where the worker is presently is created from the identified sound portions. This sound fingerprint characterizes the soundscape around the user.

In block 140, the generated sound fingerprint is compared with environmental fingerprints of known locations or activities that the user may be engaging in. For example, the sound fingerprint may be compared to location database 142, which contains environmental fingerprints of a variety of different areas, in order to identify an area around the user. Additionally, the sound fingerprint may be identified in order to identify an activity that a worker may be engaging in, by comparing it to environmental fingerprints in activity in database 144. For example, if it is detected that the worker is overheating (for example based on a heavy breathing sound, e.g.), then a PAPR air flow should be increased. The sound fingerprint may, in that example, be matched to an environmental fingerprint associated with overheating and, based on that match, the PAPR air flow rate is increased, based on settings retrieved in block 150. In another example, the use of an angle grinder is detected and the ADF of a Speedglas® is switched to grinding mode.

In block 150, a functional change is retrieved in response to the match between the sound fingerprint and an environmental fingerprint. The functional change may be specific to the environment, e.g. if "Loading Dock" is detected, then a "Loading Dock functional change" is retrieved. In some embodiments, generic functional changes are retrieved. For example, if a "Loading Dock" is tagged as a "dangerous area" then a "Dangerous" model is retrieved. Similarly, if an area is detected as "High Heat" then a "High Heat" functional change is retrieved. Functional Changes may be retrieved from a settings database 152. It is also expressly contemplated that, while examples herein describe embodiments where a single functional change is implemented based on a detected environment, that, in other embodiments, multiple changes are implemented simultaneously. For example, a radio volume may be decreased and an air flow rate of a PAPR may be increased if a High Heat environment is detected.

In block 160, the retrieved functional change is implemented. The functional change may include one or more PPE setting changes, such as volume adjustment, airflow adjustment, lights turning on or off, or any other suitable change based on the new environment. The functional change may be automatically implemented, or may be implemented based in part on user acceptance of the function change, in some embodiments. Additionally, in some embodiments the functional change is delayed until a trigger event is detected. For example, a user may be approaching a welding area, but an autodarkening function is not implemented until an arc welder is detected, or until the user is within a threshold distance of the welding area, or based on a time-delay, such as when a work-shift is expected to start. The functional change may also be editable, in some embodiments, such that a wearer of the PPE can customize their own experience. For example, a user may want PAPR airflow to increase more than a manufacturer-set functional change dictates. The user may be able to provide feedback in-situ, for example by providing an adjustment that is recorded and fed back to the database directly, or through a management system, for example an application accessible using the PPE device, using another device such as an application on a smart phone, tablet, laptop or computer. This may allow a user's personal preferences to be recorded and, in some embodiments, preferentially selected over a preset function change. For example, if a preset function change of a PAPR airflow increase is two speed settings, a user may preferentially turn the fan down one setting. The next time the same environment is detected, the system may only increase the PAPR airflow setting by one, reflecting the user preference.

In block 130, a sound fingerprint is created, which is compared to environmental fingerprints stored in a database in block 140. It is expressly contemplated that the match between a retrieved environmental fingerprint and the sound fingerprint may often not be an exact match. For example, depending on the day, an outdoor environment may have or lack wind or rain sounds, and indoor environments may have more or fewer humans talking, or more or fewer machines active. However, method 100 operates, in some embodiments, based on a most-likely-match system, such that an exact match is not required. Additionally, some noises may be disregarded in determining a match, such as weather-related sounds (which may be used only to determine that it is an 'outdoor area').

As described herein is a method of changing equipment settings based on an ambient environment around the equipment. The method includes a device operating with a first equipment setting, e.g. a first volume level, a first fan level, a first blower level, etc. An ambient sound is captured using a microphone associated with, or near to, the equipment. The ambient sound is indicative of the environment the equipment is in. The ambient sound is classified, using a sound processor, and a portion of the sound is classified. Based on the identified sounds in the captured sound, a sound fingerprint of the environment is created, which is then compared to a database of environment fingerprints. Based on the comparison, a likely environment is identified. Based on known parameters of the likely environment (temperature, air quality, danger, ambient sound levels), functionality of the equipment is automatically adjusted. For example, if the environment is a very noisy environment, level dependent functionality may be activated or adjusted. If the environment is a dangerous environment, non-necessary sounds (e.g. FM radio, music) may be reduced in volume or eliminated.

Figure 4:
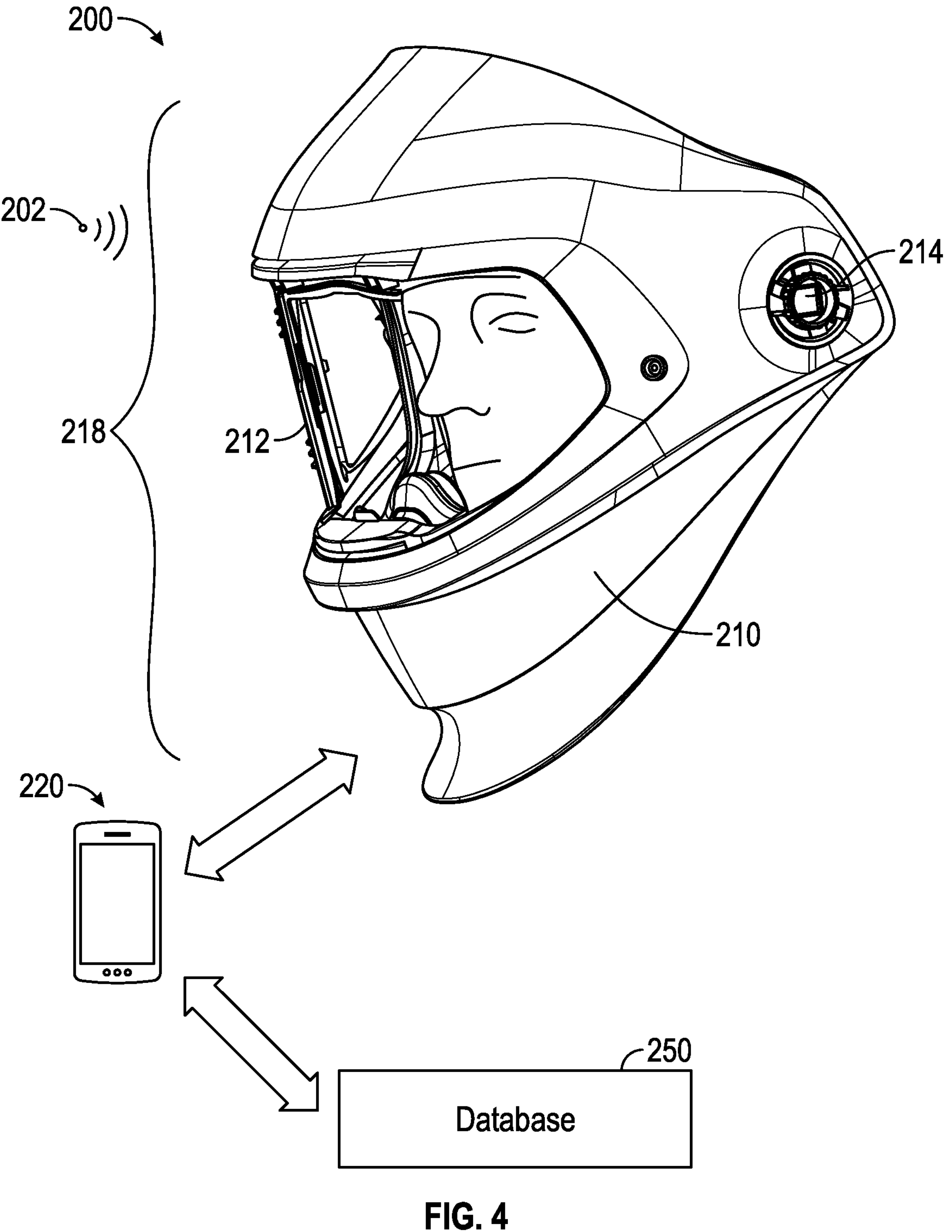
FIG. 4 illustrates a PPE sound modification system in an embodiment of the present invention.

FIG. 4 illustrates a PPE function modification system in an embodiment of the present invention. System 200 may be useful with the hearing protection devices of FIG. 1, as well as other PPE devices. For example, Welding helmet 218, illustrated in FIG. 4, may include a function modification system 220. Described in embodiments in this disclosure are function modification systems that may be suitable for a variety of PPE systems, specifically any PPE system that include a microphone that picks up ambient noise. For example, a welding helmet 218 is illustrated in FIG. 4 and helmet 218 may provide sound from a microphone to an in-ear speaker hearing protection unit, or an over-the-ear hearing protection unit worn by a user together with helmet 218. Helmet 218 may also have a microphone located on an exterior dedicated to picking up ambient environmental sound. In some embodiments, helmet 218 has an accelerometer or inertial measurement unit that can function similar to a microphone. It is also expressly contemplated that, in some embodiments, the microphone may be located remotely from welding helmet 218, for example a microphone associated with phone 220, which the user wears with them, may be the ambient sound capture device.

FIG. 4 illustrates a welding helmet 218 in a system 200 comprising head-mounted device 210, visor attachment assembly 214 and one or more microphones (not shown) on an exterior or interior surface of device 210 or on the outside of the attenuating part of the hearing protection device to capture external sounds.

As illustrated, PPE device 200 is in communicative contact with a separate device 220, illustrated in FIG. 4 as a cellphone, which may have an application through which a user or wearer of PPE device 200 may interact with a database 250 containing a number of environmental fingerprints, each with a corresponding function adjustment. However, it is expressly contemplated that, in some embodiments, a PPE may communicate directly with database 250. For example, welding helmet 200 includes a screen 212 which may have augmented reality overlay abilities. A wearer may be able to, using audio, motion, or remote controller, interact with database 250 using a processer integrated into PPE 200 using screen 212. However, many PPE devices lack a screen and are designed to reduce processing power to preserve battery life. Therefore, in many embodiments, and as described herein, PPE devices are envisioned as interacting with database 250 using an intermediate device 220.

Additionally, while a cell phone 220 is illustrated in FIG. 4, it is expressly contemplated that other computing devices 220 are possible, including laptops, tablets, desktop computers, or other computing terminals able to interact, either in a wired or wireless capacity, with both of PPE device 200 and database 250.

Computing device 220 comprising one or more computer processors and a memory comprising instructions that may be executed by the one or more computer processors. Computing device 220 is communicatively coupled to the PPE device 200 and to database 250. Computing device 220 may include the same, a subset, or a superset of functionality and components illustrated and described in other figures of this disclosure. However, as described above, in some embodiments computing device 220 is integrated into either PPE device 200 or database 250, such that device 200 communicates directly with database 250.

Computing device 220 may be included in, or attached to, an article of personal protective equipment (e.g., system 200), may be positioned on or attached to the worker in a separate device external to head top 210, or may be in a remote computing device separate from the worker altogether (e.g., a remote server or safety terminal for users). Computing device 220 may communicate with database 250 in accordance with techniques of this disclosure.

In accordance with embodiments herein, microphones (not shown) associated with PPE 200 may receive a sound stream 202, create an environment fingerprint based on identified sounds in the sound stream, and apply a function adjustment to a function of PPE 200 based on a matching environmental fingerprint in database 250.

In some embodiments, a processor responsible for recognizing sounds and applying a model may detect and identify a sound portion within sound stream 202 that is unfamiliar. The PPE processor may generate a query for database 250 regarding the unknown sound. The query may be sent via device 220, in one embodiment, either instantaneously, when device 200 is in a charging state, or when device 220 is connected to WIFI, for example. The query may be sent at other appropriate times, in other embodiments.

As described in greater detail herein, sound modification database 250 includes functionality, in some embodiments, to classify or identify sounds currently 'unknown' to the PPE processor and provide a function adjustment that can be downloaded into a local memory of PPE device 200. Alternatively, in some embodiments, the sound recognition process is done using a processor of device 220. Other suitable configurations are also possible.

Figures 11A, 11B, 11C, 11D:
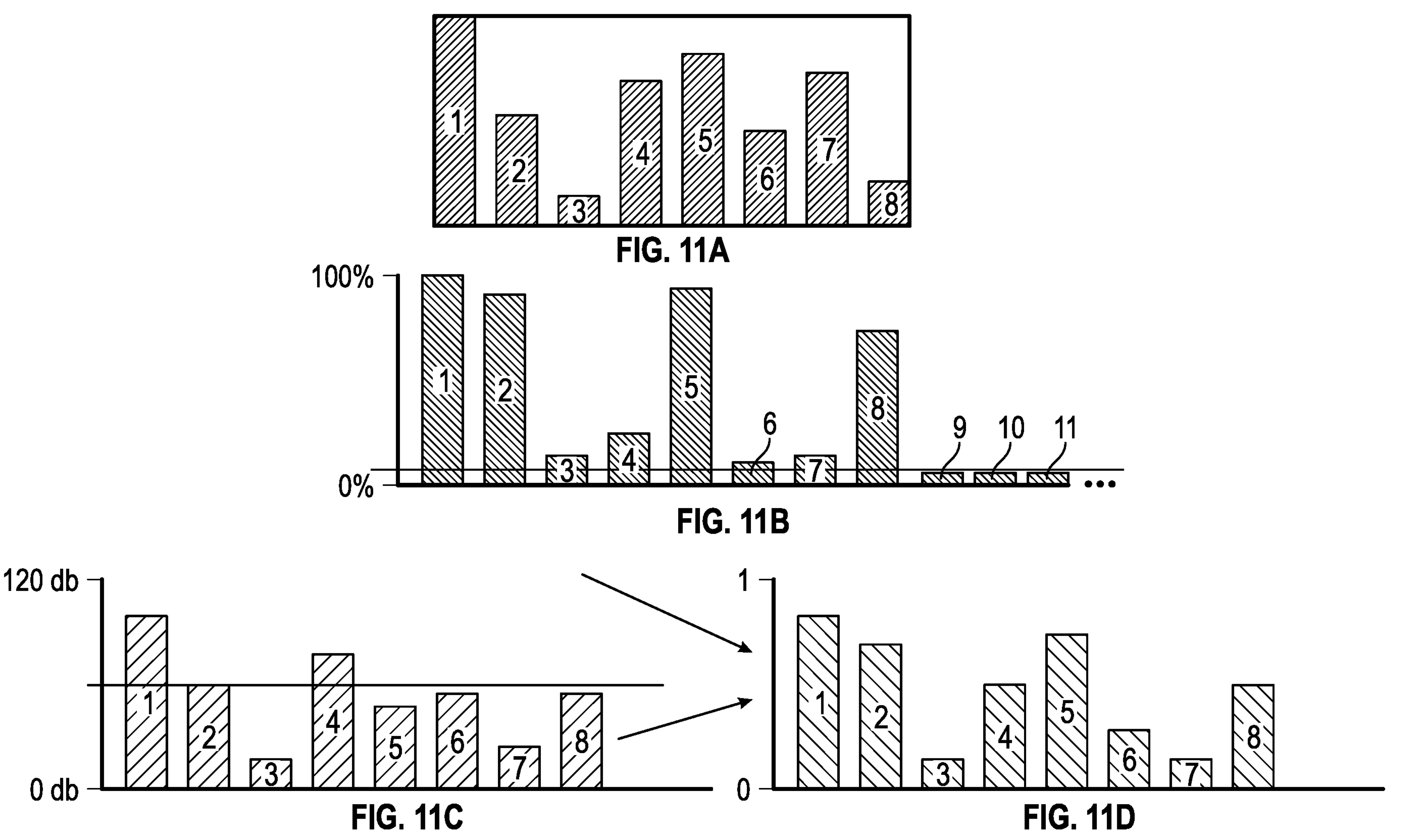
FIGS. 11A-11D illustrate an example extraction and validation of an identified sound object.

An unknown sound could be identified, if the classification process illustrated in FIG. 11B comes up with a rather unspecific classification (low contribution across all used classes or no significant differentiation between classes). In order to improve detection of unknown sounds, a sample of this unknown sound is recorded and saved on the PPE device for upload to the model database at a suitable point in time (charging, connectivity).

A backend service may take new, previously unknown sounds together with known sounds and train a new model or algorithm that is capable of separating the different sounds from each other. Training can be done incrementally or from scratch. A new model will be deployed to the PPE device together with the new fingerprints as a new model revision.

In some embodiments, at least some steps of method 100 are accomplished using a processor of device 220. In other embodiments, method 100 is accomplished solely using processors and memory integrated into device 200.

Described herein, in some embodiments, are systems and methods that are capable of providing alerts in response to certain recognized sounds or environmental fingerprints. Said alerts can be provided using audio, visual or haptic feedback mechanisms within PPE 200 and/or using audio, visual or haptic feedback mechanisms of computing device 220. Additionally, in some embodiments either PPE device 200 or computing device 220 may store or send indications of generated alerts to another remote device or storage medium.

Computing device 220 may generate any type of indication of output. In some examples, the indication of output may be a message that includes various notification data. Notification data may include but is not limited to: an alert, warning, or information message: a type of personal protective equipment: a worker identifier: a timestamp of when the message was generated: a position of the personal protective equipment: one or more light intensities, or any other descriptive information. In some examples, the message may be sent to one or more computing devices as described in this disclosure and output for display at one or more user interfaces of output devices communicatively coupled to the respective computing devices. In some examples computing device 220 may receive an indication of where a sound source originated (e.g. based on a communication from a device generating a recognized sound) and generate the indicated output further based on the sound source and sound type was occurring.

Figure 5A:
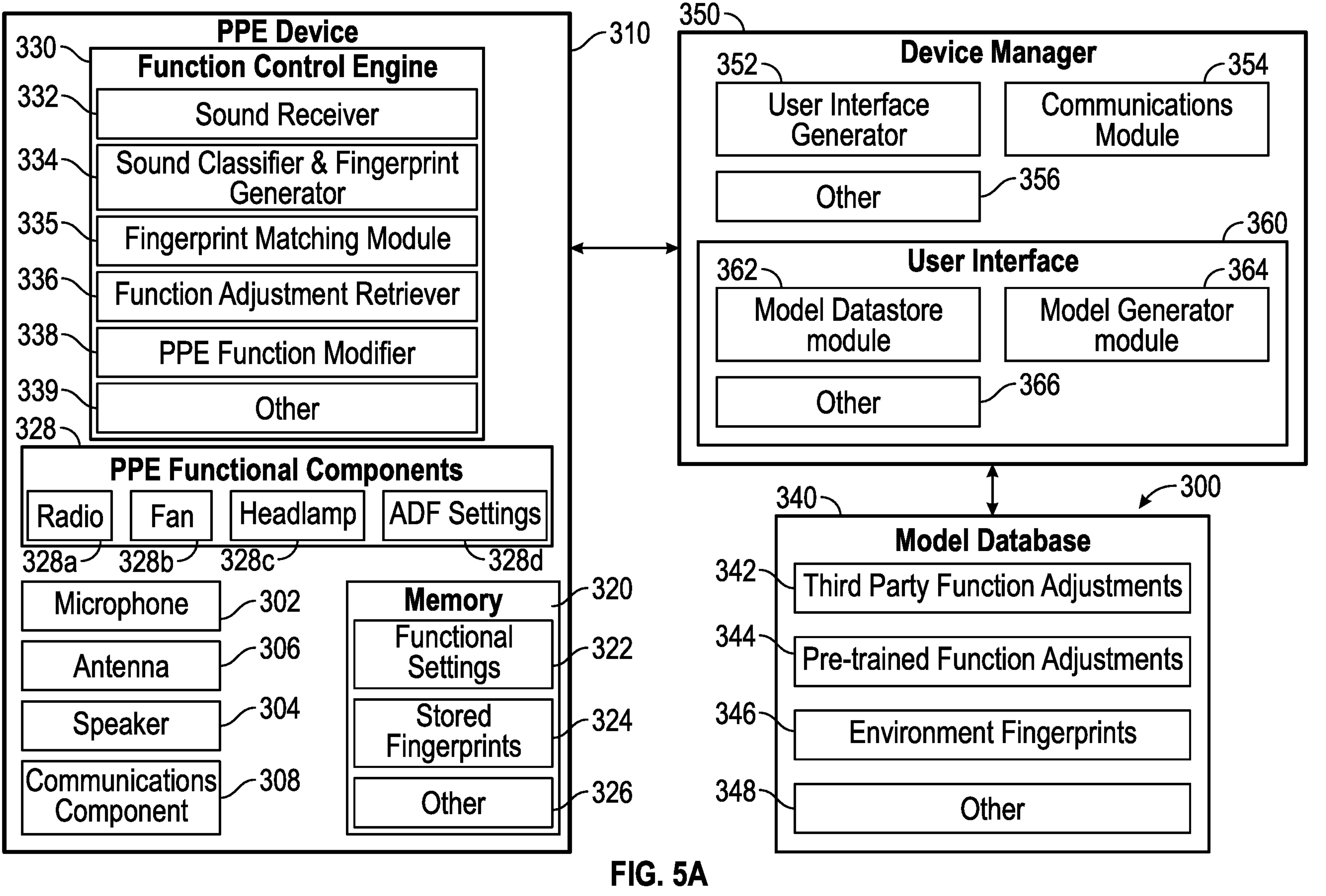
FIGS. 5A-5B illustrate schematics of a sound model management system in an embodiment of the present invention.
Figure 5B:
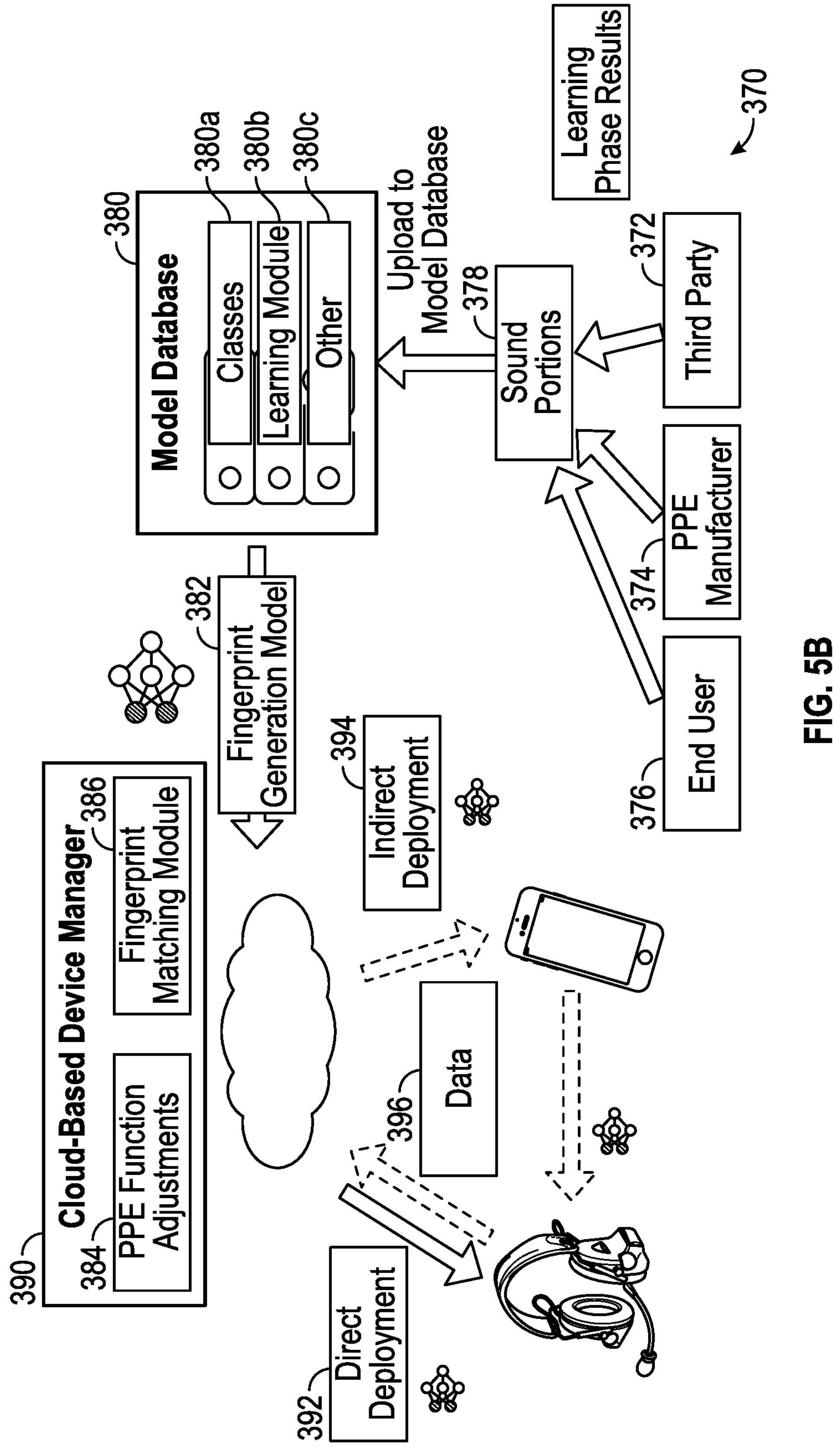

FIGS. 5A and 5B illustrate a schematic of a PPE device interacting with a function adjustment management system in an embodiment of the present invention. System 300 represents interactions of a single PPE device 310 with database 340. However, as contemplated in FIG. 2, it is expressly contemplated that systems and methods described herein may operate in a networked environment with other PPE devices 310 all accessing a single model database 340.

In the embodiment illustrated in FIG. 5A, PPE device 310 accesses database 340 via device manager 350. However, in other embodiments, it is expressly contemplated that PPE device 310 may interact with database 340 directly such that at least some of the functionality of device manager 350 is incorporated into PPE device 310.

PPE device 310 includes one or more microphones 302 configured to pick up environmental sounds. PPE device 310 may also include one or more antenna 306 configured to receive signals from other devices, including other PPE devices 310, including audio signals that may be treated similarly to, or incorporated into an ambient sound stream received by microphone 302. PPE device also includes one or more speakers 304 configured to broadcast sound to a wearer of PPE device 310. PPE device may also include a communications component 308 configured to communicate with device manager 350, or directly with database 340.

PPE device 310 also includes a memory 320 which stores, among other data 326 necessary for the functional operation of PPE device 310, and stored functional settings 322.

PPE device also includes function control engine 330 that analyzes ambient environmental sounds and adjusts functional settings as needed to improve an experience for a wearer of PPE device 310 by automatically adjusting settings of functional components 328 based on a detected environment, activity or task. For example, volume of radio 328*a* may be turned up or down based on whether hazards are present in an ambient environment, or increasing/decreasing a fan based on an indication that the wearer is in a hot environment. Similarly, an auto-darkening feature or a headlamp 328*c* may be activated based on an indication that grinding is ongoing nearby.

Sound receiver 332 receives a sound stream from a microphone 302. Sound fingerprint generator 334 identifies sounds within the sound stream and characterizes the combination of sounds as a sound fingerprint. Sound fingerprint generator 334 recognizes several independent classes within the sound portion, creating the fingerprint by combining the contributions from the different classes and the respective sound pressure levels. Fingerprint matching module 335, compares the sound fingerprint to stored fingerprints 324, to find a match. In some embodiments, finding a match includes finding a best match, or finding a match within a preset threshold. When a match is found, fingerprint adjustment retriever 336 retrieves a stored functional adjustment 322 and applies it to a functional setting of PPE device 310. Because the construction zone was identified, a volume of radio 328*a* may be reduced so that the wearer of PPE 310 may be more aware of potential nearby hazards. A speed of fan 328*b* may be increased if the construction zone is known to be outside with a high temperature. PPE function modifier 338 may apply a functional change based on a degree of confidence in the match between a sound fingerprint and an environmental fingerprint 324. For example, the degree of confidence may vary between a minimum of 85-95% confidence.

PPE function modifier 338 generates and sends control signals to PPE functional components 328 to implement the functional changes.

Function control engine 330 may also have other functionality. For example, function control engine 330, in some embodiments, sends a query to database 340 when a sound portion is unrecognized.

PPE device 310 can be one of any suitable PPE devices that includes a microphone or other device that captures ambient sound. PPE device may be a hearing protection device such as over-ear or in-ear hearing protection units. PPE device may also be a PAPR respirator, a welding helmet, or any other suitable PPE embodiment. PPE device 310 include any functional components 328 that are necessary for said personal protection function.

Database 340 stores environmental fingerprints and associated function adjustments that can be accessed using a suitable interface. In some embodiments, PPE device 310, using function control engine 330, may directly interface with database 340 to retrieve new functional adjustments as needed, and/or to provide an unrecognized sound for analysis. Database 340 may include functional adjustments from a variety of places. For example, a manufacturer of PPE device 310 may provide pre-trained functional adjustments 344 based on expected interactions with different locations, activities and environments. For example, a manufacture of military hearing protection device may generate a variety of functional adjustments based on anticipated environments such as outdoor vs indoor environments, while a manufacture of a welding helmet may generate a variety of functional adjustments based on the sound of welding torches in different environments or the use of power tools in-between welding operations. Additionally, third parties may upload third-party functional adjustments 342. For example, an individual owner of a PPE device may upload the sound of a saws-all cutting through PVC pipe, and may want active hearing protection increased whenever the sound of a saws-all is detected in a sound fingerprint. Additionally, a manufacturer of power tools may upload a variety of models that can be activated based on different power tools acting on different materials in different environments.

Database 340 may also include other data or functionality 348 in accordance with methods and systems described herein.

Device manager 350 is illustrated in FIG. 5 as separate from PPE device 310 and database 340. In some embodiments, device manager 350 communicates with PPE device 310 using a wireless network such as WIFI, cellular network, Bluetooth®, NFC, or other suitable communication protocol. However, in other embodiments, device manager 350 requires a wired connection. Device manager 350 may communicate with database 350, for example, using wireless, cellular, or cloud-based communication networks. Device manager 350 communicates with PPE device 310 and database 340 using one or more communications module 354. Device manager 350 may also include other suitable functionality 356.

Device manager 350 may be any suitable computing device such as a cellular phone, tablet, laptop computer, desktop computer, or other device. Device manager 350 has a screen configured to display a user interface 360, generated by user interface generator 352 based on a user actuating a function management application. The user interface 360 may provide a user a way to view environmental fingerprints and functional adjustments available for download to a PPE device 310 through datastore module 362, which may also indicate stored functional adjustments 322 stored on device 310 already. A user may add or remove functional adjustments to database 322 using a datastore module, and may associate functional changes with stored environmental fingerprints 324. Additionally, user interface 360 may present a functional adjustment generator module 364, which may allow for a user to generate a new functional adjustment 342, for example based on a recorded sound, which may form the basis of environment fingerprint. The recorded sound may be uploaded directly from PPE device 310, device manager 350, or from PPE device 310 via device manager 350. Additional environmental fingerprints 346 may also be uploadable, for example recordings of known or unknown sounds captured on a device other than PPE device 310. User interface 360 may also include other features or icons.

For example, a plurality of environmental fingerprints 346 may be uploaded along with location information.

Personal protective equipment devices are described herein. A PPE device includes a microphone that captures a sound stream indicative of an ambient environment. Based on the sound stream, a fingerprint representative of the ambient environment is created. Based on the fingerprint, a function adjustment is selected. The function adjustment is then applied by an equipment trigger that adjusts a functional setting of the PPE device.

FIG. 5B illustrates another embodiment of a function adjustment management system 370. A database 380 may receive sound samples from a variety of sources including, but not limited to a PPE device manufacturers 374, third parties 372, or end-users 376, either an individual or an enterprise using PPE devices. A source 372, 374, 376 may provide a sound sample 378 to a model database 380, for example through a wired or wireless network connection. Sound portions 378 may be full environmental fingerprints, or sounds that may be heard in different environments, or sounds that are recorded separately and under controlled conditions, and be incorporated into a specific environmental fingerprint by fingerprint generation module 382.

Database 380 may store classes of sounds 380*a*, for example vehicle sounds, construction sounds, hazard sounds, or other classes of sounds 380*a* that may indicate a particular environment, activity or task. Sounds associated with classes 380*a* may be sample portions 378 provided by a PPE manufacturer as a separated sound or (to be mixed with existing environmental sounds 380*c* for model training) or an estimation of how a sound may be experienced in an environment, or an actual recorded sound sample provided by an end user 376 and stored in database 380.

A learning module 380*b* may also be housed in database 380. Learning module 380*b* may improve fingerprint generation model 382 over time by learning which classes 380*a* contribute to different environments or areas.

Fingerprint generation module 382 may generate sample environment fingerprints that are provided to a cloud-based device manager 390. A number of potential PPE functional adjustments 384 may be stored in cloud-based device manager 390. However, it is expressly contemplated that functional adjustments 384 may also be stored in database 380, and tied to environmental fingerprints when generated, in other embodiments. Similarly, a fingerprint matching module 386 may match an ambient environment fingerprint to that generated by fingerprint generation module 382 and, based on a match, select a suitable PPE function adjustment 384.

As illustrated in FIG. 5B, a PPE device may provide data 396, for example telemetry data, location data, ambient sound samples or user data, back to cloud-based device manager 390. In some embodiments a review process to ensure quality, safety and reliability of the environmental fingerprint matching module 386 might be performed prior to providing the new environmental fingerprints to the device manger 390.

Cloud-based device manager 390 may also have other functionality, for example communicating information to a plurality of PPE devices, in embodiments such as FIG. 2 where a PPE device is one of many within a network. In other embodiments, where a lone user of a PPE device interacts with model database 380, cloud-based device manager 390 may be accessed indirectly 394 using an application on a computing device.

Cloud-based device manager may provide fingerprint matching module 386 and PPE functional adjustments 384, along with fingerprints generated by fingerprint generation module 382, to a device either using direct deployment 392, or indirectly, using indirect deployment 394 through an intermediate device. Indirect deployment 394 may provide the benefit of allowing a user of a PPE device to select generated environmental fingerprints that are more relevant to them. For example, a user may expect to wear PPE inside a pilot plant. The user may, therefore, not need environmental fingerprints relevant to construction worksites. Alternatively, cloud-based device manager 390 may receive a batch of environmental fingerprints and associated function adjustments from a safety manager of the pilot plant, including, for example, sound portions 378 captured within the pilot plant, optionally along with desired PPE function adjustments 384 when each environmental area is detected.

A method of processing sound in a personal protective equipment device is enabled by the system 300. The PPE device is able to receive an ambient sound stream and identify, based on the first ambient sound stream, a first work environment by comparing the fingerprint of the ambient sound stream to fingerprints made by fingerprint generation module, using fingerprint matching module. A first functional setting change is retrieved based on the identified first work environment, for example from PPE function adjustments 384, which may be downloaded from a database or stored on the PPE device. The first functional setting change is automatically applied to the personal protective equipment device. For example, the PPE device may reduce a volume of FM radio if the identified first work environment has potential hazards.

The PPE device may receive a second ambient sound stream at a second time and identify, based on the fingerprint of the second ambient sound stream, a second work environment different from the first work stream, for example using fingerprint matching module 386 to compare against a fingerprint generated by fingerprint generation model 382. A second functional setting change may be retrieved, for example a second PPE function adjustment 384, based on the identified second work environment. The second functional setting change may be automatically applied to the personal protective equipment device. For example, a second work environment may be detected as a smelting area. FM radio may be returned to its original volume, and a fan of a PAPR may be turned on, or a fan speed increased, to ensure that the worker does not overheat.

FIG. 5B illustrates a distributed embodiment for retrieving new environment fingerprints and associated PPE function adjustments. However, it is expressly contemplated that, in most operation, a PPE device has its own fingerprint matching module, a database of stored environmental fingerprints and associated PPE function adjustments such that functional settings may be adjusted in situ without a need to communicate with a device manager 390 or a separate database 380. PPE device may communicate with a device manager 390, and/or database 380, in such embodiments, during a charging period or another period when connection is made, either wired or wirelessly, either direct or indirect through the computing device.

Figure 6:
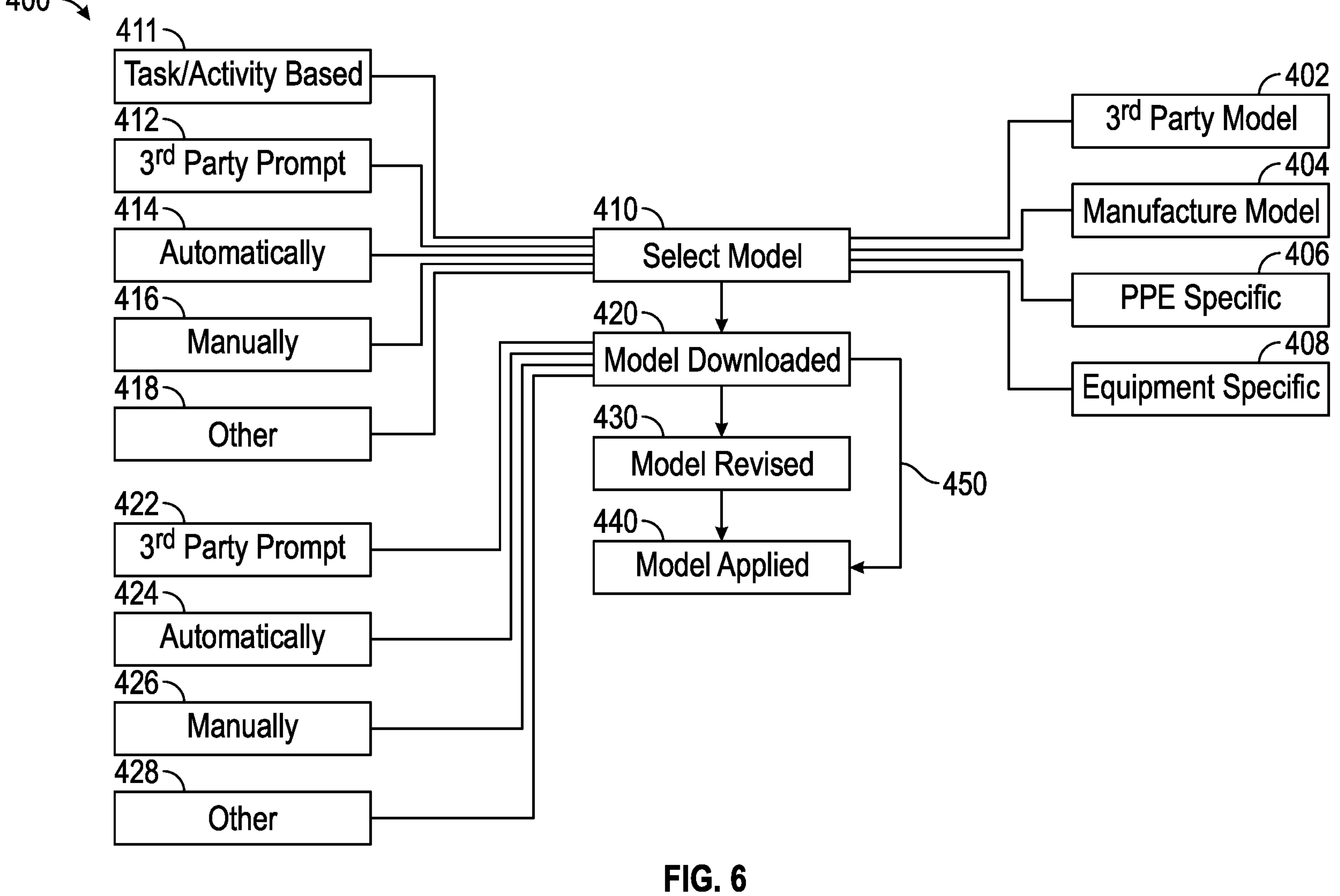
FIG. 6 illustrates a method of obtaining a new sound model for a PPE device in an embodiment of the present invention.

FIG. 6 illustrates a method of obtaining a new environmental fingerprint and associated functional adjustment for a PPE device in an embodiment of the present invention. Selecting an environmental fingerprint, as used with respect to method 400, may include selecting a preset environmental fingerprint, where, for example, a functional setting is preset with respect to an environment. However, in some embodiments, a user may be able to adjust or select a functional setting to implement with respect to a selected environmental fingerprint. Such functionality may be limited to some users, for example by safety officers, to ensure worker safety is maintained.

Method 400 may be used to apply newly available or newly relevant environmental fingerprints. For example, a worker may be transferred to a different worksite with different environmental fingerprints. The environmental fingerprints of the first worksite may be removed, and those relevant to the new worksite may be retrieved using method 400. Method 400 may be practiced by a user interacting with a download application, for example on a mobile phone or directly on a PPE device, optionally using a screen on the PPE device.

In block 410, using a user interface, a user selects a relevant environmental fingerprint. The environmental fingerprint may be provided from a PPE device manufacturer 404, a 3rd party 402 or another suitable source. The environmental fingerprint may be specific to a PPE device, for example to reduce the sound of a PAPR respirator through a functional setting of a hearing protection device, or may be equipment-specific, such as to increase a fan speed if a hot environment is detected through characteristic equipment sounds.

The new environmental fingerprint may be selected automatically 414—for example, when a device is connected to a database and new or updated environmental fingerprints relevant to the user are available. Alternatively, the environmental fingerprint may be selected manually 416. Environmental fingerprints may be downloaded individually, for example a new environmental fingerprint recently captured for a smelting area with new equipment, or as a bundle, for example all environmental fingerprints for Worksite A. Additionally, a 3rd-party prompt 412 may indicate that the user should download a relevant environmental fingerprint. For example, an equipment manufacturer may provide a QR-code that, when scanned by a user's phone, selects fingerprints and/or function presets relevant to the equipment. Other methods of selecting a model are also expressly contemplated.

In block 420, an environmental fingerprint is downloaded to the PPE device. In one embodiment, the environmental fingerprint is s downloaded directly to the PPE device from a database. In another embodiment, the environmental fingerprint is downloaded to the PPE device through a hub, such as a mobile phone. The environmental fingerprint may be downloaded based on a prompt from a 3rd-party 422, automatically based on availability, for example, as indicated in block 424, manually, as indicated in block 426, or based on another suitable trigger 428.

As indicated by arrow 450, in some embodiments, an environmental fingerprint or a function preset is ready to be applied by a PPE device, as indicated in block 440 to incoming sound when downloaded. However, as indicated in block 430, in some embodiments the environmental fingerprint or functional setting is revised prior to its use. For example, a computational device, such as a mobile phone, laptop, tablet or desktop computer, may allow a PPE device user to revise an environmental fingerprint or associated functional adjustment prior to its application. For example, downloading an environmental fingerprint 420 may refer to the step of downloading the environmental fingerprint from a cloud-based database to an intermediate hub device, such as mobile device 220, which then can provide the environmental fingerprint or functional setting, in a second step, to PPE device 200.

In block 430, a selected environmental fingerprint is revised, either while stored in the cloud-based model database, while stored on an intermediate hub device, or after downloaded to a memory of a PPE device. For example, an end user may be able to update a stored environmental fingerprint with the ambient environmental fingerprint.

One option to (initially) train the system, is that a designated person, for example a production supervisor uses the PPE device in a training mode, optionally using a mobile device 220, recording sound portions 378 to generate environmental fingerprints and associated functional settings for the relevant areas, task or activities to be stored in the device manager 390. From the device manager 390, the relevant environmental fingerprints and functional settings are then deployed at a later stage to the respective PPE users on that worksite as described above. To improve the system performance, retraining or adjustments might be required over time. One way of doing that could be notifying a PPE wearer of detected fingerprints and ask for confirmation. For example, when a fingerprint that is related to a smelting area is detected, the worker is notified with “smelting area detected”. The worker can confirm or reject that detection. In a second example, the user can be offered to decide between different environments. In a third example the user can label an environment with a new label or associate with an environment, activity or task from a predefined list. This way the system can improve over time with feedback from users.

However, while environmental fingerprints are discussed herein as being generated or revised, it may be preferred that the generation or revision take place on a device other than the PPE device, as the software size requirements could be prohibitive for a PPE device.

Figure 7:
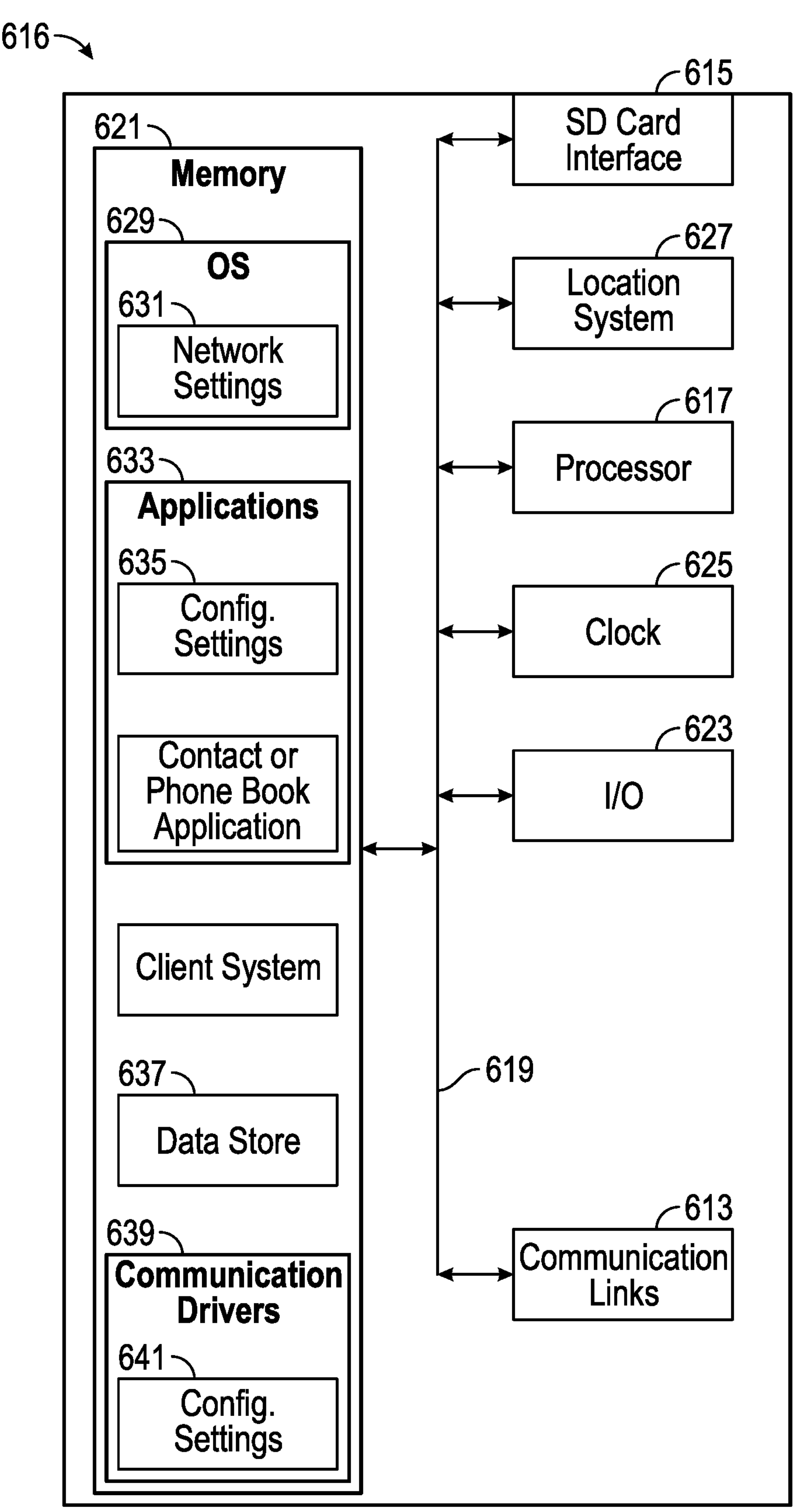
Figure 8:
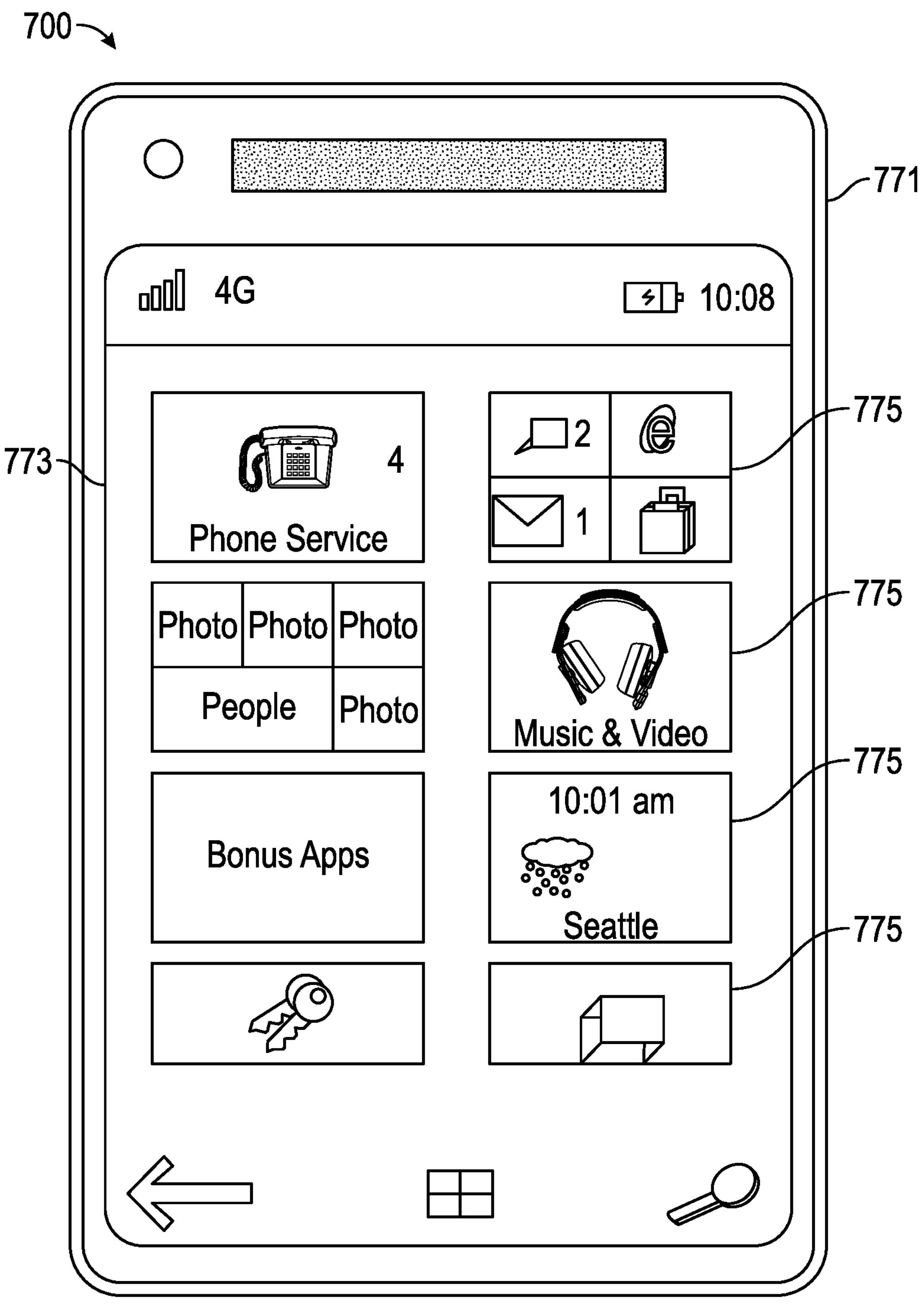

FIGS. 7-9 illustrate example devices that can be used in the embodiments shown in previous Figures. FIG. 7 illustrates an example mobile device that can be used in the embodiments shown in previous Figures. FIG. 7 is a simplified block diagram of one illustrative example of a handheld or mobile computing device that can be used as either a worker’s device or a supervisor/safety officer device, for example, in which the present system (or parts of it) can be deployed. For instance, a mobile device can be deployed in the operator compartment of computing device for use in generating, processing, or displaying the data.

FIG. 7 provides a general block diagram of the components of a mobile cellular device 616 that can run some components shown and described herein. Mobile cellular device 616 interacts with them or runs some and interacts with some. In the device 616, a communications link 613 is provided that allows the handheld device to communicate with other computing devices and under some embodiments provides a channel for receiving information automatically, such as by scanning. Examples of communications link 613 include allowing communication though one or more communication protocols, such as wireless services used to provide cellular access to a network, as well as protocols that provide local wireless connections to networks.

In other examples, applications can be received on a removable Secure Digital (SD) card that is connected to an interface 615. Interface 615 and communication links 613 communicate with a processor 617 (which can also embody a processor) along a bus 619 that is also connected to memory 621 and input/output (I/O) components 623, as well as clock 625 and location system 627.

I/O components 623, in one embodiment, are provided to facilitate input and output operations and the device 616 can include input components such as buttons, touch sensors, optical sensors, microphones, touch screens, proximity sensors, accelerometers, orientation sensors and output components such as a display device, a speaker, and or a printer port. Other I/O components 623 can be used as well.

Clock 625 illustratively comprises a real time clock component that outputs a time and date. It can also provide timing functions for processor 617.

Illustratively, location system 627 includes a component that outputs a current geographical location of device 616. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 621 stores operating system 629, network settings 631, applications 633, application configuration settings 635, data store 637, communication drivers 639, and communication configuration settings 641. Memory 621 can include all types of tangible volatile and non-volatile computer-readable memory devices. It can also include computer storage media (described below). Memory 621 stores computer readable instructions that, when executed by processor 617, cause the processor to perform computer-implemented steps or functions according to the instructions. Processor 617 can be activated by other components to facilitate their functionality as well. It is expressly contemplated that, while a physical memory store 621 is illustrated as part of a device, that cloud computing options, where some data and/or processing is done using a remote service, are available.

FIG. 8 shows that the device can also be a smart phone 771. Smart phone 771 has a touch sensitive display 773 that displays icons or tiles or other user input mechanisms 775. Mechanisms 775 can be used by a user to run applications, make calls, perform data transfer operations, etc. In general, smart phone 771 is built on a mobile operating system and offers more advanced computing capability and connectivity than a feature phone. Note that other forms of the devices are possible.

FIG. 9 is one example of a computing environment in which elements of systems and methods described herein, or parts of them (for example), can be deployed. With reference to FIG. 9, an example system for implementing some embodiments includes a general-purpose computing device in the form of a computer 810. Components of computer 810 may include, but are not limited to, a processing unit 820 (which can comprise a processor), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to systems and methods described herein can be deployed in corresponding portions of FIG. 9.

Computer 810 typically includes a variety of computer readable media. Computer readable media can be any available media that can be accessed by computer 810 and includes both volatile/nonvolatile media and removable/non-removable media. By way of example, and not limitation, computer readable media may comprise computer storage media and communication media. Computer storage media is different from, and does not include, a modulated data signal or carrier wave. It includes hardware storage media including both volatile/nonvolatile and removable/non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810.

Communication media may embody computer readable instructions, data structures, program modules or other data in a transport mechanism and includes any information delivery media. The term "modulated data signal" means a signal that has one or more of its characteristics set or changed in such a manner as to encode information in the signal.

Figure 10:
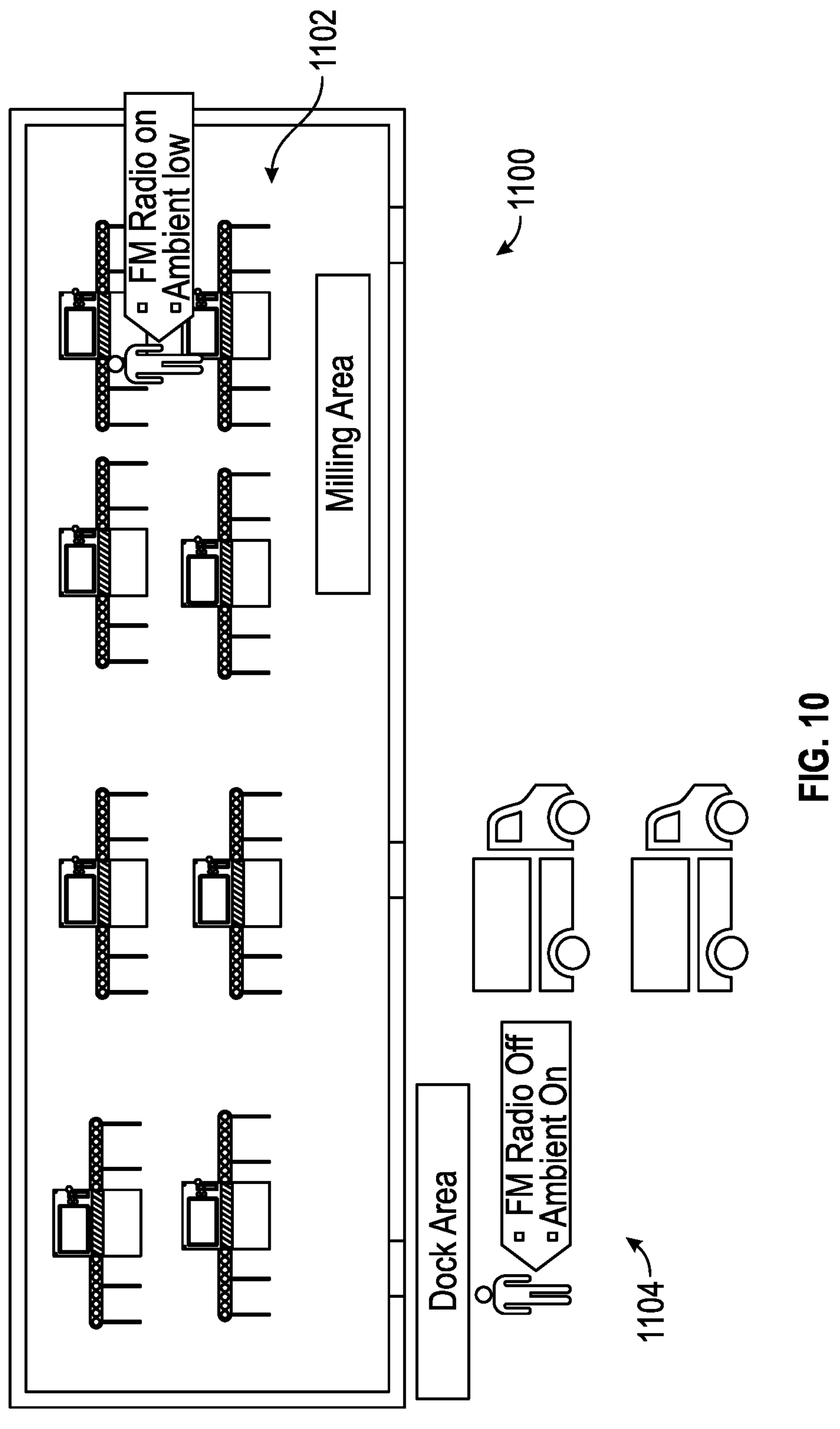
FIG. 10 illustrates an example user interface structure that may be used in embodiments herein.

The system memory 830 includes computer storage media in the form of volatile and/or nonvolatile memory such as read only memory (ROM) 831 and random-access memory (RAM) 832. A basic input/output system 833 (BIOS) containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable and volatile/nonvolatile computer storage media. By way of example only, FIG. 10 illustrates a hard disk drive 841 that reads from or writes to non-removable, nonvolatile magnetic media, nonvolatile magnetic disk 852, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 9, provide storage of computer readable instructions, data structures, program modules and other data for the computer 810. In FIG. 13, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite receiver, scanner, a gesture recognition device, or the like. These and other input devices are often connected to the processing unit 820 through a user input interface 860 that is coupled to the system bus but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections, such as a Local Area Network (LAN) or Wide Area Network (WAN) to one or more remote computers, such as a remote computer 880. The computer may also connect to the network through another wired connection. A wireless network, such as WiFi may also be used.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

A personal protective equipment device is presented. The PPE device includes a microphone configured to capture an ambient sound stream. The PPE device also includes a sound analyzer that receives the ambient sound stream and characterizes a sound fingerprint around the device based on the ambient sound stream. The PPE device also includes a function preset selector that, based on the characterized sound fingerprint, selects a function preset. The PPE device also includes a function preset implementor that implements the function preset in response to an event trigger. Implementing the function preset includes adjusting a functional setting of a device from a first setting to a second setting.

The device may be implemented such that the sound fingerprint is characterized as one of a known hot location. The function preset is a higher volume of airflow through a blower unit, and the function preset implementor adjusts a blower setting of a PAPR unit from a first setting to a second setting.

The device may be implemented such that the event trigger includes the PPE device entering the hot location, identified by the respective sound fingerprint, and the second setting is a higher volume flow rate than the first setting.

The device may be implemented such that the device is a welding helmet, the sound fingerprint is characterized as including an arc welding task. The function preset includes adjusting a functional setting of the welding helmet from a first setting to a second setting.

The device may be implemented such that the event trigger is immediately the functional setting is a darkness of the welding helmet, and the second setting is a darker setting than the first setting.

The device may be implemented such that the identified sound fingerprint represents a first identified environment, location or task identified in the ambient sound stream.

The device may be implemented such that the identified sound fingerprint also represents a second identified environment, location or task identified in the ambient sound stream.

The device may be implemented such that the event trigger includes an immediate implementation of the function preset.

The device may be implemented such that the event trigger includes a delayed implementation of the function preset.

The device may be implemented such that the function preset implementation is delayed until an event is detected.

The device may be implemented such that the detected event includes a location of the PPE device, an environment, location or task; a newly detected environment, location or task, the absence of the former, or an indication from a user of the PPE device.

The device may be implemented such that it also includes a fingerprint database including a plurality of environment fingerprints, location fingerprints and task fingerprints and a function preset database including a plurality of function presets, each function preset being correlated with one of the plurality of environment fingerprints, location fingerprints or task fingerprints.

The device may be implemented such that the fingerprint database or the function preset database is stored in a memory of the PPE device.

The device may be implemented such that the function preset selector compares the sound fingerprint with the plurality of environmental, location and task fingerprints in the fingerprint database and if the sound fingerprint is within a match threshold to one of the plurality of fingerprints in the database, selects a corresponding function preset.

The device may be implemented such that the function preset implementor, based on the function preset and previous preset state, adjusts a functional setting of the PPE device itself or another device.

The device may be implemented such that the PPE device is a hearing protection device, the sound fingerprint includes an indication of a welding tool and the sound fingerprint is within a match threshold to a welding task, and the function preset adjusts a functional setting of a welding helmet to darken a darkness setting of the welding helmet.

The device may be implemented such that the PPE device is a hearing protection device, the sound fingerprint includes a vehicle sound, the sound fingerprint is within a match threshold to a loading zone, and the function preset adjusts a volume setting of the hearing protection device to reduce the volume of an FM radio.

The device may be implemented such that the ambient sound is a first ambient sound captured at a first time, the device captures a second ambient sound at a second time. The sound analyzer characterizes a second sound fingerprint based on the second ambient sound. The function preset selector, based on the second sound fingerprint, selects a second function preset. The function implementor, based on the second function preset, a current function state and an event trigger, adjusts a second functional setting of a device.

The device may be implemented such that the second functional setting is different from the first functional setting.

The device may be implemented such that the sound analyzer analyzes the captured sound stream continuously, and the function preset selector is activated if the second sound fingerprint differs from the sound fingerprint by more than a threshold fingerprint variation.

The device may be implemented such that continuously includes sampling the captured sound screen using a windowed sample method.

The device may be implemented such that a first window overlaps with a second window.

The device may be implemented such that a first window includes one second of the captured sound stream.

The device may be implemented such that a first window includes a half second of the captured sound stream.

The device may be implemented such that a first window is distinct from a second window.

The device may be implemented such that a space between the first window and the second window is dynamically selected.

The device may be implemented such that the fingerprint database is communicably coupled to a remote database including a plurality of downloadable fingerprints.

The device may be implemented such that the function preset database is communicably coupled to a remote database including a plurality of downloadable function presets.

The device may be implemented such that the PPE device has a speaker, and the function preset includes a volume adjustment.

The device may be implemented such that PPE device has a fan, and the function preset includes a fan speed adjustment.

The device may be implemented such that the function preset includes an alert, and the alert includes audio, visual or haptic feedback.

The device may also include a communications component configured to receive a function preset or identifiable fingerprint from a second device.

The device may be implemented such that the communications component operates under a 2.4 GHz protocol or a 5 GHz protocol.

The device may be implemented such that the device is a hearing protection device, and the hearing protection device provides level dependent hearing protection.

The device may be implemented such that the hearing protection device is an in-ear hearing protection device.

The device may be implemented such that the hearing protection device is an over-ear headset.

The device may be implemented such that the device is a powered air purifying respirator.

The device may be implemented such that the device is a welding helmet.

The device may be implemented such that the welding helmet includes a hearing protection component.

The device may be implemented such that the sound analyzer detects a sound indicative of a moving vehicle. The sound fingerprint includes the moving vehicle indication.

The device may be implemented such that the function preset includes a decreased volume of device-provided sound.

The device may be implemented such that the sound analyzer detects a sound indicative of a smelter, and the sound fingerprint includes the smelter indication.

The device may be implemented such that the function preset includes an increased fan speed.

The device may be implemented such that the function preset include an alert activation.

The device may be implemented such that the sound fingerprint includes an indication of injury, and the event trigger is immediately.

The device may be implemented such that a function preset selector selects, based on the characterized sound fingerprint, multiple function presets that fit to the characterized sound fingerprint and a function preset implementor implements one or more of the function presets in response to an event trigger and a prioritization order of the function presets. Implementing the function preset or presets includes adjusting a functional setting of at least one device from a first setting to a second setting.

A method of adjusting a function setting of a personal protective equipment device is presented. The method includes receiving, using a sound receiver, a first ambient sound stream. The method also includes characterizing, using a sound analyzer, based on the first ambient sound stream, a first sound fingerprint around the PPE device based on the ambient sound stream. The method also includes retrieving, using a function preset selector, a first functional setting from a database based on the characterized sound fingerprint. The method also includes adjusting, using a PPE function preset implementor, a functional setting of the PPE device to the first functional setting. The functional setting is adjusted in response to an event trigger.

The method may also include receiving a second ambient sound stream and characterizing, based on the second ambient sound stream, a second sound fingerprint around the PPE device based on the ambient sound stream, and retrieving, using the function preset selector, a second functional setting from the database based on the characterized sound fingerprint, and adjusting, using a PPE function modifier, the functional setting of the PPE device to the second function setting. The functional setting is adjusted in response to a second event trigger.

The method may be implemented such that the event trigger is immediately.

The method may be implemented such that the event trigger is a time delay.

The method may be implemented such that the event trigger is a detection of a sound received later than the first ambient sound stream.

The method may be implemented such that the event trigger is a command.

The method may be implemented such that the command is received in response to a notification or question.

The method may be implemented such that characterizing the sound fingerprint includes identifying a sound in the sound stream and, generating the sound fingerprint based on the identified sound, and matching the sound fingerprint to an environment fingerprint.

The method may be implemented such that the environment fingerprint is based on a previous recording of the first work environment.

The method may also include associating the first ambient sound stream with a first time. The first time is indicative of when the first ambient sound stream is captured. The method also includes associating the second ambient sound stream with a second time. The second time is indicative of when the second ambient sound stream is captured.

The method may also include generating a first indication that the PPE device is in the first environment, at the first time, based on the identified first environment, and a second indication that the PPE device is in the second environment, at the second time, based on the identified second environment.

The method may also include communicating, using a communication module, the first and second indication to a second device.

The method may be implemented such that the second device associates the first and second indications with a first and second location, respectively, of the PPE device within a worksite.

The method may be implemented such that the second device, based on the indicated location, adjusts a functional setting or initiates an action.

The method may also include communicating the functional setting to the PPE device from a device separate from the PPE device.

The method may be implemented such that retrieving the first functional setting change includes:

comparing the characterized sound fingerprint to an environmental fingerprint, and if a match is detected, the function preset selector retrieving the first functional setting change. The first functional setting change is associated with the environmental fingerprint.

The method may be implemented such that the functional setting is communicated wirelessly.

The method may be implemented such that the first and second ambient sound streams are received through a microphone positioned on an exterior of the personal protection device.

The method may be implemented such that the first and second ambient sound streams are received through a microphone positioned on an interior of the personal protective device.

The method may be implemented such that the first and second ambient sound streams are received through a solid-borne sound collection system.

The method may be implemented such that the solid-borne sound collection system is an accelerometer.

The method may be implemented such that the first and second ambient sound streams are received by a device remote from the personal protective equipment device.

The method may be implemented such that the personal protective equipment device is an in-ear hearing protection device, an over-ear hearing protection device, a welding helmet or a powered air purifying respirator.

The method may be implemented such that the personal protective equipment device is a hearing protection device. The first functional setting is a decrease of a speaker volume from a current volume to a lower volume.

The method may be implemented such that the personal protective equipment device is a powered air purifying respirator. The first functional setting is an increase in fan speed from a current fan speed to a higher fan speed.

The method may be implemented such that the steps of identifying, retrieving and applying are done automatically when a new ambient sound stream is received.

The method may be implemented such that a new ambient sound stream is received periodically.

The method may be implemented such that a new ambient sound stream is received intermittently.

A method of changing equipment settings on a device is presented. The method also includes operating a function of the device at a first function setting. The method also includes receiving an ambient sound stream from a microphone in an area of a worksite. The method also includes characterizing a sound fingerprint of the ambient sound stream, using a sound analyzer. The method also includes matching the sound fingerprint to an environmental fingerprint, using a matching module, by comparing the sound fingerprint to a database of environmental fingerprints. The method also includes retrieving a functional change for the device, using a function model retriever. The functional change is a second function setting for the function of the device. The functional change is retrieved based on a match of the sound fingerprint to an environmental fingerprint associated with the functional change. The method also includes applying the functional change such the device changes from the first function setting to the second function setting.

The method may be implemented such that the device is a personal protective equipment device.

The method may be implemented such that the device is a hearing protection device, and the first equipment setting is a first volume setting, and the second equipment setting is a second volume setting, and the second volume setting is lower than the first volume setting.

The method may be implemented such that the area has been labeled as a hazardous area.

The method may be implemented such that the sound is a vehicle sound.

The method may be implemented such that the area is a loading dock.

The method may be implemented such that the area has been labeled as a hot area.

The method may be implemented such that the device is a personal air purifying respirator, the first equipment setting is a first fan setting, the second equipment setting is a second fan setting, and the second setting is higher than the first setting.

The method may be implemented such that the sound is associated with equipment known to be in the hot area.

The method may be implemented such that the environmental fingerprint includes an activity.

The method may be implemented such that the activity is arc welding.

The method may be implemented such that the functional change is a darkening of a face shield, and the second function setting is a less dark setting than the first function setting.

The method may be implemented such that the functional change is immediately implemented.

The method may be implemented such that the functional change is delayed until the device is within a minimum distance of the arc welding activity.

The method may be implemented such that the microphone is associated with a second device.

The method may be implemented such that applying the functional change includes sending a command to the device to change from the first function setting to the second function setting.

The method may be implemented such that applying the functional change includes the device automatically adjusting the function to the second functional setting.

The method may also include communicating an indication of area position of the device to a second device.

The method may be implemented such that the indication is communicated with a timestamp, and the timestamp is a time the sound was received, or identified or classified, or the adjustment to the second function setting was applied.

The method may be implemented such that characterizing the ambient sound stream includes: identifying an area or a task based on the identified sound fingerprint.

The method may be implemented such that matching the sound fingerprint to an environmental fingerprint includes searching the database for an environmental fingerprint with the identified area or task.

EXAMPLES

Example 1: Milling Worksite

FIG. 10 illustrates a worksite 1100 with a milling machine in a first environment 1102, and a loading dock in a second area 1104. The milling machine is on, and the trucks illustrated in the loading dock are moving.

When entering the dock area, the outside microphones of a hearing protection device will continue to record the outside sound. A sound classifier will classify portions of the environment sound. The sound stream will contain several portions with different magnitude—one of the portions will be the truck movements. The combination of the individual portions form the fingerprint of the loading dock 1104 at the moment they are recorded.

The system then searches to find the closest matching fingerprint(s) in an environment fingerprint database. The closest matching fingerprint in the database matches the location of the wearer. The area is identified as the loading dock 1104.

The headset then applies settings stored for this locations, such as turning down a Volume of FM radio and increasing a Volume of outside sound so that the wearer is able to hear approaching vehicles.

When the worker later moves from dock area 1104 to the production area 1102, the outside microphones of the hearing protection, which are continuing to record the outside sound, detect the new sound. Continuing to record may refer to the hearing protection unit sampling ambient sound periodically at an adjustable frequency (for example more frequently in areas or around activities indicated as dangerous, or in response to a steep increase in sound pressure level). A time slicing method may also be used, in some embodiments. Additionally, sampling can be done with a low frequency or a dynamically adjusted frequency. Sampling could be triggered by noise (For example reacting to a steep increase in sound pressure), or a sampling frequency could be increased in response to a noise trigger. The sound analyzer receives the ambient sound stream and characterizes a sound fingerprint out of the ambient sound stream. A sound fingerprint consists of characteristics of individual sound sources or superpositions or combinations thereof.

The sound analyzer may be capable of analyzing the incoming sound stream from a microphone. In some embodiments, the sound analyzer receives and analyzes the incoming sound stream continuously. In some embodiments, the sound analyzer receives the incoming sound stream continuously but samples and analyzes periodically. For example, the sound analyzer may use a window sampling method, selecting a first window of sound (e.g. 1-10 seconds) for analysis and, at a different time, selecting a second window of sound for analysis. The first and second windows may be the same amount of time (e.g. both 5 seconds), or may be different amounts of time. The first and second windows of time may be distinct (e.g. seconds 1-5 in the first window and seconds 7-11 in the second window) or may overlap (e.g. seconds 1-5 in the first window and seconds 4-8 in the second window). Additionally, a time selection for the second window may be based on the analysis of the first window. For example, a loud sound may trigger a more frequent sampling. Alternatively, repeated consistent sound may trigger less frequent sampling. However, based on the analysis of a given window, a function present selector is activated if it is detected that the user is in a new environment, e.g. if a sound fingerprint associated with a second sampling window differs enough from a sound fingerprint associated with a first sampling window.

In the given example, the sound of the milling machine will have a significant impact on the fingerprint of that area.

The system then searches to find the closest matching fingerprint(s) in the environmental fingerprint database. The closest matching fingerprint in the database will be assumed as the current location of the wearer. In the given example, the area is assumed as the milling area 1102.

The headset will now apply settings stored for this location, such as increasing a Volume of the FM radio and decreasing the level of ambient sound.

Example 2: Task/Activity Detection Speedglas Welding Helmet

Given:

Speedglas™ Welding Helmet with auto-darkening-filter (ADF) and microphone to record environmental sound Welding machine Angle grinder Workflow:

1. While welding operation, the outside microphones of the welding helmet will continue to record the outside sound.
2. The sound classifier will classify the portions of the environment sound. The sound stream will contain several portions with different magnitude—one of the portions will be the sound typically associated with the welding operation. This is illustrated in FIGS. 11A-11D. FIG. 11A illustrates the environmental sound stream that includes at least 8 different sounds. A threshold may be applied, as illustrated in FIG. 11B, such that only sounds above a threshold are considered. The Y-axis illustrates a percent certainty of sound class identification. Sounds that have a low likelihood of identification may be discarded. In FIG. 11C, the sound pressure levels of sound portions 1-8 are illustrated, which are above the threshold mentioned in FIG. 11B.
3. The combination of the percent certainty of the individual classified portions that are above a threshold with a given sound pressure of those portions are used to form a weighted class pattern that becomes the fingerprint of that area at this moment (FIG. 11D). Further combinations are possible
4. The system will now find the closest matching fingerprint(s).
5. The closest matching fingerprint matches the assumed task or activity of the wearer to be welding operation.
6. The welding helmet will now apply settings stored for this activity or task, such as applying a specific setting (e.g. darkening level or sensitivity setting) to the ADF.
7. When changing from welding operation to another task, e.g. the use of an angle grinder to prepare the next welding line or to finish a welding line just made, the outside microphones of the welding protection will continue to record the outside sound.
8. The sound classifier will classify the portions of the environment sound. The sound stream will contain several portions with different magnitude—one of the portions will be the angle grinder.
9. The combination of the individual portions form the fingerprint of that area at this moment.
10. The system will now find the closest matching fingerprint(s).
11. The closest matching fingerprint matches the assumed task or activity of the wearer.
12. The welding helmet will now apply settings stored for this activity or task of using an angle grinder, such as setting the ADF shade 3 to avoid the sparks of the grinding activate the higher shade level needed for welding.

Example 3: Peltor® Control of Speedglas

Given:

Peltor® hearing protection with level-dependent-function (LDF) and connected PPE communication capabilities (e.g. BLE, WiFi)

Speedglas Welding Helmet with auto-darkening-filter (ADF) and connected PPE communication capabilities (e.g. BLE, WiFi)

Welding machine

Angle grinder

Workflow:

1. Peltor® hearing protection and Speedglas welding helmet are connected through a connected PPE communication protocol (e.g. via Bluetooth Low Energy (BLE))
2. While welding operation, the outside microphones of the Peltor® hearing protection will continue to record the outside sound.
3. The sound classifier will classify the portions of the environment sound. The sound stream will contain several portions with different magnitude—one of the portions will be the sound typically associated with the welding operation.

4. The combination of the individual portions form the fingerprint of that area at this moment.
5. The system will now find the closest matching fingerprint(s).
6. The closest matching fingerprint matches the assumed task or activity of the wearer to be welding operation.
7. The headset will now send a command to apply settings to the connected welding helmet stored for this activity or task, such as applying a specific setting (e.g. darkening level or sensitivity setting) to the ADF.
8. When changing from welding operation to another task, e.g. the use of an angle grinder to prepare the next welding line or to finish a welding line just made, the outside microphones of the hearing protection will continue to record the outside sound.
9. The sound classifier will classify the portions of the environment sound. The sound stream will contain several portions with different magnitude—one of the portions will be the angle grinder.
10. The combination of the individual portions form the fingerprint of that area at this moment.
11. The system will now find the closest matching fingerprint(s).
12. The closest matching fingerprint matches the assumed task or activity of the wearer.
13. The headset will now send a command to apply settings to the connected welding helmet that are stored for this activity or task of using an angle grinder, such as setting the ADF shade 3 to avoid the sparks of the grinding activate the higher shade level needed for welding.

As a sub-set of what is described above, one might decide to only detect situations of non-welding tasks, as welding requires higher shade level from the beginning, even prior to generating characteristical sound.

What is claimed is:

1. A personal protective equipment (PPE) device comprising:

a microphone configured to capture an ambient sound stream;

a sound analyzer that receives the ambient sound stream and characterizes a sound fingerprint around the device based on the ambient sound stream;

a function preset selector that, based on the characterized sound fingerprint, selects a function preset that specifies a functional change for the device; and a function preset implementor that implements the function preset in response to an event trigger, wherein implementing the function preset comprises adjusting a functional setting of a device from a first setting to a second setting; setting wherein the sound fingerprint is characterized as a known hot location by matching the sound fingerprint to an environmental fingerprint labeled as the known hot location in a fingerprint database, the environmental fingerprint including a sound indicative of equipment known to be in the hot location; wherein the function preset is a higher volume of airflow through a blower unit of a powered air purifying respirator (PAPR), and the function preset implementor adjusts a blower setting from the first setting to the second setting, the second setting being a higher airflow setting; and wherein the event trigger comprises the PPE device entering the hot location identified by the sound fingerprint.

2. The device of claim 1, wherein the device is a welding helmet, the sound fingerprint is characterized as comprising an arc welding task, and wherein the function preset comprises adjusting a functional setting of the welding helmet from a first setting to a second setting.

3. The device of claim 1, wherein the identified sound fingerprint represents a first identified environment, location or task identified in the ambient sound stream.

4. The device of claim 1, and further comprising:

a fingerprint database comprising a plurality of environment fingerprints, location fingerprints and task fingerprints; and a function preset database comprising a plurality of function presets, each function preset being correlated with one of the plurality of environment fingerprints, location fingerprints or task fingerprints.

5. The device of claim 4, wherein the function preset selector compares the sound fingerprint with the plurality of environmental, location and task fingerprints in the fingerprint database and if the sound fingerprint is within a match threshold to one of the plurality of fingerprints in the database, selects a corresponding function preset.

6. The device of claim 1, wherein the ambient sound is a first ambient sound captured at a first time, and wherein the device captures a second ambient sound at a second time, and wherein:

the sound analyzer characterizes a second sound fingerprint based on the second ambient sound;

the function preset selector, based on the second sound fingerprint, selects a second function preset, and the function implementor, based on the second function preset, a current function state and an event trigger, adjusts a second functional setting of a device.

7. The device of claim 1, wherein the function preset database is communicably coupled to a remote database comprising a plurality of downloadable function presets.

8. The device of claim 1, wherein the function preset comprise an alert activation.

9. The device of claim 8, wherein the sound fingerprint comprises an indication of injury, and wherein the event trigger is immediately.

10. A method of adjusting a function setting of a personal protective equipment (PPE) device, the method comprising:

receiving, using a sound receiver, a first ambient sound stream;

characterizing, using a sound analyzer, based on the first ambient sound stream, a first sound fingerprint around the PPE device; device based on the ambient sound stream;

identifying the first sound fingerprint as a known hot location by matching the first sound fingerprint to an environmental fingerprint labeled as the known hot location in a fingerprint database, the environmental fingerprint including a sound indicative of equipment known to be in the hot location;

retrieving, using a function preset selector, a first functional setting from a database based on the characterized first sound fingerprint, the functional setting being a higher volume of airflow through a blower unit of a powered air purifying respirator (PAPR);

and fingerprint;

adjusting, using a PPE function preset implementor, the functional setting of the PPE device to the from a first functional setting, wherein the functional airflow setting specifies to a functional change for the PPE device, wherein the functional second airflow setting that is adjusted higher than the first airflow setting, in response to an event trigger comprising the PPE device entering the hot location identified by the first sound fingerprint, trigger.

11. The method of claim 10, and further comprising:

receiving a second ambient sound stream;

characterizing, based on the second ambient sound stream, a second sound fingerprint around the PPE device based on the ambient sound stream;

retrieving, using the function preset selector, a second functional setting from the database based on the characterized sound fingerprint;

adjusting, using a PPE function modifier, the functional setting of the PPE device to the second function setting, wherein the functional setting is adjusted in response to a second event trigger.

12. The method of claim 10, wherein the first and second ambient sound streams are received through a microphone positioned on an exterior or an interior of the personal protection device.

13. The method of claim 10, wherein the first and second ambient sound streams are received through a solid-borne sound collection system.

14. The method of claim 10, wherein the steps of identifying, retrieving and applying are done automatically when a new ambient sound stream is received.

15. A method of changing equipment settings on a device, the method comprising:

operating a function of the device at a first function setting;

receiving an ambient sound stream from a microphone in an area of a worksite;

characterizing a sound fingerprint of the ambient sound stream, stream using a sound analyzer;

matching the sound fingerprint to an environmental fingerprint, fingerprint using a matching module, module by comparing the sound fingerprint to a database of environmental fingerprints;

identifying the environmental fingerprint as a known hot location by matching the sound fingerprint to an environmental fingerprint that includes a sound indicative of equipment known to be in the hot location;

retrieving a functional change for the device, retrieving, using a function model retriever, wherein a functional change associated with the hot location, the functional change being a second function fan-airflow setting for the function of the device, a powered air purifying respirator (PAPR) blower unit, and wherein the functional change is retrieved based on being a match of the sound fingerprint to an environmental fingerprint associated with higher airflow setting than the first function setting; and functional change;

applying the functional change by sending control signals to functional components of the device such that the device changes from the first function setting to the second function setting in response to the device entering the hot location identified by the sound fingerprint, setting.

16. The method of claim 15, wherein the device is a personal protective equipment device.

17. The method of claim 15, wherein applying the functional change comprises the device automatically adjusting the function to the second functional setting.

18. The method of claim 15, and further comprising:

communicating an indication of area position of the device to a second device.

* * * * *